US006694047B1

United States Patent
Farrokhnia et al.

(10) Patent No.: US 6,694,047 B1
(45) Date of Patent: Feb. 17, 2004

(54) METHOD AND APPARATUS FOR AUTOMATED IMAGE QUALITY EVALUATION OF X-RAY SYSTEMS USING ANY OF MULTIPLE PHANTOMS

(75) Inventors: Farshid Farrokhnia, Brookfield, WI (US); Kenneth Scott Kump, Waukesha, WI (US); Richard Aufrichtig, Moutain View, CA (US); Alexander Y. Tokman, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/354,389

(22) Filed: Jul. 15, 1999

(51) Int. Cl.[7] ................................................ G06K 9/00
(52) U.S. Cl. ........................ 382/132; 378/20; 378/64; 378/163; 378/177; 378/205; 378/207; 382/131; 382/151; 382/195; 382/283; 600/414; 600/426
(58) Field of Search .................. 378/20, 163, 204–207; 382/132, 283, 131, 151, 195, 199, 203; 600/414, 426

(56) References Cited

U.S. PATENT DOCUMENTS

| | | | |
|---|---|---|---|
| 4,126,789 A | | 11/1978 | Vogl et al. |
| 5,276,726 A | | 1/1994 | Galkin |
| 5,299,253 A | * | 3/1994 | Wessels ...................... 378/163 |
| 5,406,612 A | * | 4/1995 | Galkin ........................ 378/207 |
| 5,481,587 A | | 1/1996 | Mazess |
| 5,511,107 A | * | 4/1996 | Sliski ......................... 378/207 |
| 5,539,799 A | | 7/1996 | Schulze-Ganzlin et al. |
| 5,544,238 A | | 8/1996 | Galkin |
| 5,651,046 A | | 7/1997 | Floyd et al. |
| 5,841,835 A | * | 11/1998 | Aufrichtig et al. ........... 378/207 |
| 5,892,840 A | * | 4/1999 | Jang et al. ................... 382/132 |
| 6,018,590 A | * | 1/2000 | Gaborski ..................... 382/168 |
| 6,148,095 A | * | 11/2000 | Prause et al. ................ 382/131 |
| 6,231,231 B1 | * | 5/2001 | Farrokhnia et al. .......... 378/207 |
| 6,370,480 B1 | * | 4/2002 | Gupta et al. .................. 702/39 |
| 6,405,072 B1 | * | 6/2002 | Cosman ....................... 600/426 |
| 6,409,383 B1 | * | 6/2002 | Wang et al. .................. 378/207 |
| 6,473,659 B1 | * | 10/2002 | Shah et al. .................... 700/79 |

* cited by examiner

Primary Examiner—Bhavesh M. Mehta
Assistant Examiner—Gregory Desire
(74) Attorney, Agent, or Firm—McAndrews, Held & Malloy, Ltd.; Peter J. Vogel; Michael A. Dellapenna

(57) ABSTRACT

A system for automated x-ray system parameter evaluation is provided. A physical model or template is created and stored in the system, one for each desired phantom. The automated system imports a grayscale x-ray image and then processes the image to determine image components. First, a histogram of the image is created, then a threshold in the histogram is determined and the imported image is binarized with respect to the threshold. Next, connected component analysis is used to determine image components. If the components do not match, then the image is rejected. The system next locates landmarks in the imported image corresponding to expected physical structures. The landmarks include a perimeter ring, vertical and horizontal line segments, and fiducials. The system uses the landmarks to predict Regions of Interest (ROIs) where measurement of the x-ray system parameters takes place. Finally, the x-ray system parameters are measured in the identified ROIs.

34 Claims, 18 Drawing Sheets

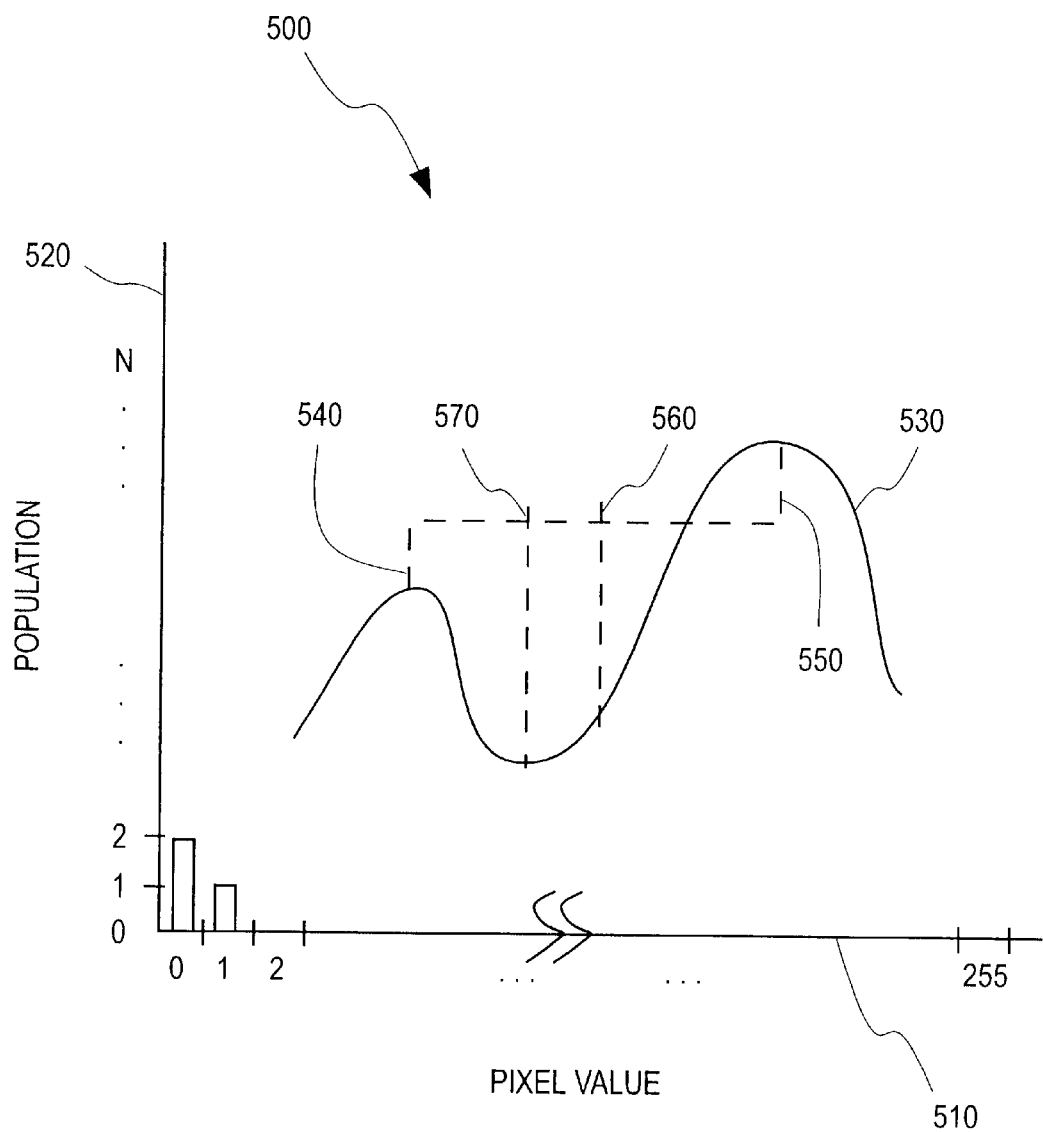

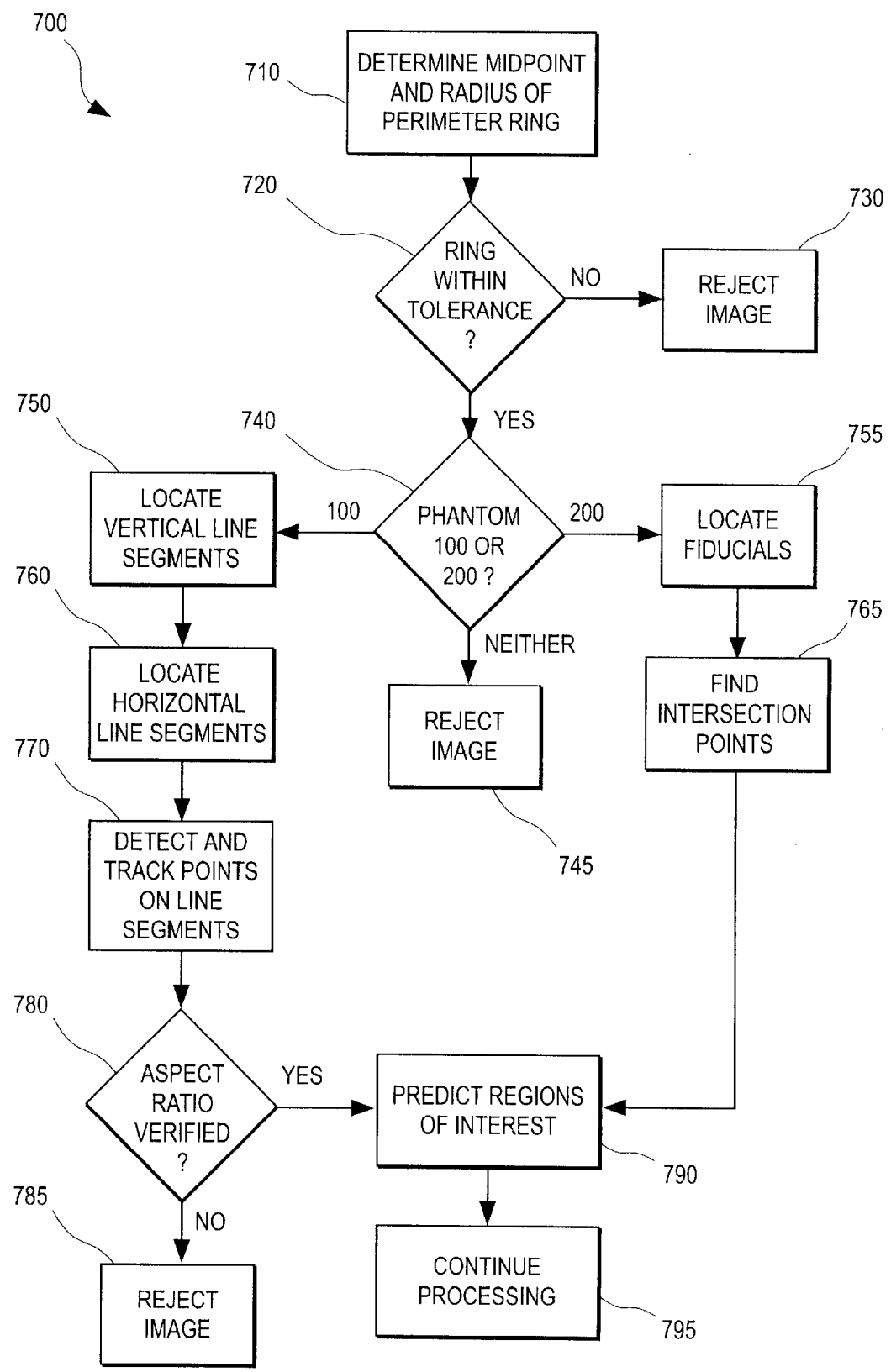

100

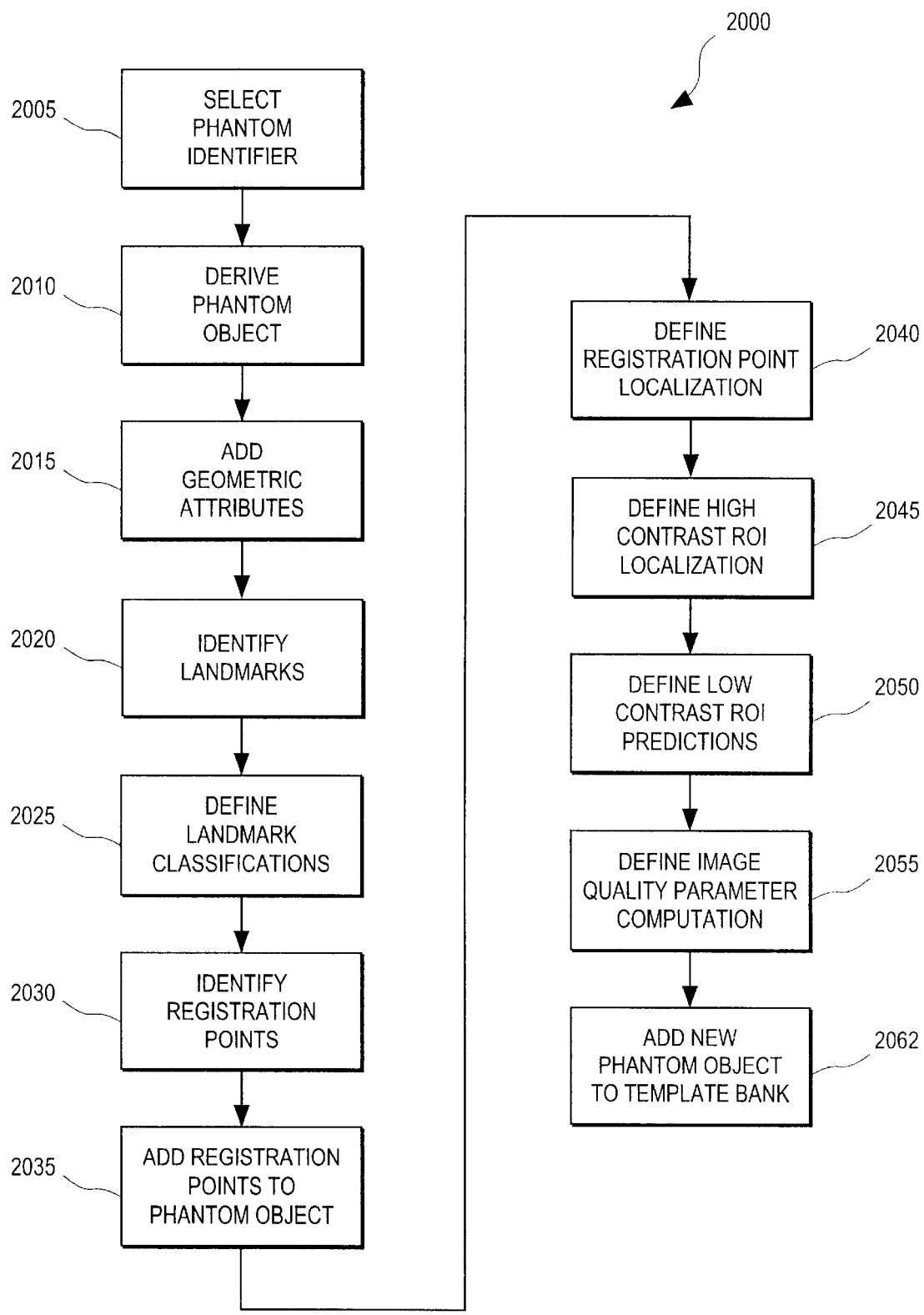

METHOD AND APPARATUS FOR AUTOMATED IMAGE QUALITY EVALUATION OF X-RAY SYSTEMS USING ANY OF MULTIPLE PHANTOMS

BACKGROUND OF THE INVENTION

The present invention generally relates to an automated system for evaluating image quality of x-ray systems. More particularly, the present invention relates to an automated analysis and measurement of image quality parameters of an x-ray system using one or more x-ray phantoms. Also, the present invention provides automated Region Of Interest (ROI) determination to facilitate image quality parameter measurement.

X-ray systems, such as an image intensifier, storage phosphor plates or digital detectors, typically include an x-ray emitter and an x-ray receiver. A target to be viewed, such as a human body, is arranged between the x-ray emitter and the x-ray receiver. X-rays produced by the emitter travel through the target to reach the receiver. As the x-rays travel from the emitter through the target, internal components of the target may decrease the energy of the x-rays to varying degrees through effects such as the blocking or absorption of some of the x-rays. The blocking or absorption of x-rays within the target causes the received x-ray energy levels to vary. The x-ray receiver receives the x-rays which have traveled through the target. An image of the target is generated at the x-ray receiver. The image produced at the receiver contains regions of light and dark which correspond to the varying intensity levels of the x-rays which have passed through the target.

The x-ray images may be used for many purposes. For instance, internal defects in the target may be detected. Additionally, changes in internal structure or alignment may be determined. Furthermore, the image may show the presence or absence of objects in the target. The information gained from x-ray imaging has applications in many fields, including medicine and manufacturing.

In order to help ensure that x-ray images may be used reliably, it is advantageous to measure and verify the performance of x-ray systems. In particular, it is important to measure and verify the image quality of the x-ray system. Poor image quality may prevent reliable analysis of the x-ray image. For example, a decrease in image contrast quality may yield an unreliable image that is not usable. Additionally, the advent of real-time imaging systems has increased the importance of generating clear, high quality images. X-ray systems with poor or degraded image quality must be re-calibrated to provide a distinct and usable representation of the target.

The verification of x-ray system performance is also important for safety reasons. For example, exposure to high levels of x-ray energy may involve some health risk to humans. Because of the health risk, governmental standards are set for the use of x-ray systems. The level of x-ray energy emitted by an x-ray system may be measured in terms of radiation dosage. Periodic performance evaluation of x-ray systems may ensure that the radiation dosage to which the target is exposed does not exceed regulatory standards.

One device that may be used in the measurement of x-ray system parameters, such as image quality and radiation dosage, is an x-ray phantom. Several types of phantoms exist, including physical replica phantoms and physics-based phantoms. For example, a physical replica phantom may be a physical replica of an x-ray target, such as a human body part. A physics-based phantom may be comprised of various structures affixed to a common base. The structures of a physics-based phantom may possess varying characteristics, such as shape, size, density, and composition. Furthermore, the structures of physics-based phantoms may be constructed from various materials, including metal and plastic.

The structures of physics-based phantoms may affect the intensity of the x-rays which pass through the physics-based phantom. For example, metal structures may block some or most of the x-rays. Additionally, plastic structures may merely provide minimal attenuation of the x-rays. A pattern resulting from the changes in the intensity of received x-rays is represented in an x-ray image. The resulting pattern in the x-ray image may be easy to detect and analyze due to factors such as the contrast produced by the difference in received x-ray intensities.

Currently known phantoms may serve a variety of purposes. For example, phantoms may test performance parameters of the x-ray system. Also, phantoms, combined with radiation probes, may be used to gauge the radiation dosage of x-ray energy emitted by the emitter. Furthermore, phantoms may be used for calibration and image quality assessment.

Typically, physics-based phantoms may be designed to measure one or more parameters of an x-ray system. Different phantoms may produce different patterns of x-ray intensity or attenuation. The different patterns of x-ray intensity or attenuation may be used to measure or test different performance parameters of the x-ray system.

One of the more recent applications of phantoms is as part of a software based evaluation tool. Such a software based tool is disclosed in U.S. Pat. No. 5,841,835 issued to Aufrichtig et al. ("Aufrichtig"). Aufrichtig has a software component that may add in the assessment and calibration of an x-ray system. Iterative calibration tests may be performed using the software component. The results of iterative calibration tests performed by the software component may be compiled to show analysis, such as trending and aggregation, of the results of the x-ray system calibration tests. As iterative calibration of an x-ray system continues, the software component may automatically adjust the x-ray system parameters.

However, the Aufrichtig software component assumes that a particular phantom is being used for measuring image quality parameters of the x-ray system. If a plurality of phantoms are used, the software may need to be manually configured to react to each different phantom. The extra step of configuring the software component for each x-ray phantom may reintroduce additional human interaction in measurements. Additionally, the configuration of the software component for each x-ray phantom may increase the amount of time necessary to measure the image quality of an x-ray system.

Thus, a need has long existed for an image quality evaluation system able to automatically determine image components on any of multiple phantoms. Additionally, a need has long existed for an automated image quality evaluation system that provides self-alignment and measuring. Additionally, a need has long existed for an automated, cost-effective system for measuring critical image quality parameters using any of multiple phantoms. The preferred embodiments of the present invention address these needs and other concerns with past systems.

SUMMARY OF THE INVENTION

A method and apparatus are provided for automated x-ray system parameter evaluation. A grayscale x-ray image is imported to an image processor which processed the image to determine image components. A histogram of the image is created, then a threshold in the histogram is determined and the imported image is binarized with respect to the threshold. Next, connected component ("blob") analysis is used to determine image components. The image components in the imported image are then compared to a phantom template of expected components. The system next locates landmarks in the imported image corresponding to expected physical structures. The landmarks may include a perimeter ring, vertical and horizontal line segments, and fiducials. The system uses the landmarks to locate Regions of Interest (ROIs) where measurement of the x-ray system parameters takes place. Finally, the x-ray system parameters are measured in the identified ROIs. A coupon sub-phantom may be used to measure the horizontal or vertical Modulation Transfer Function (MTF).

These and other features of the present invention are discussed or apparent in the following detailed description of the preferred embodiments of the present invention.

BRIEF DESCRIPTION OF THE DRAWINGS

FIG. 5 illustrates a plot of an exemplary image histogram according to a preferred embodiment of the present invention.

FIG. 7 illustrates a flowchart of a preferred embodiment for locating phantom landmarks according to the present invention.

FIG. 20 illustrates a flowchart 2000 of a preferred embodiment of a system for adding a phantom template to a database or bank of phantom templates according to the present invention.

DETAILED DESCRIPTION OF THE PREFERRED EMBODIMENTS

Figure 1:
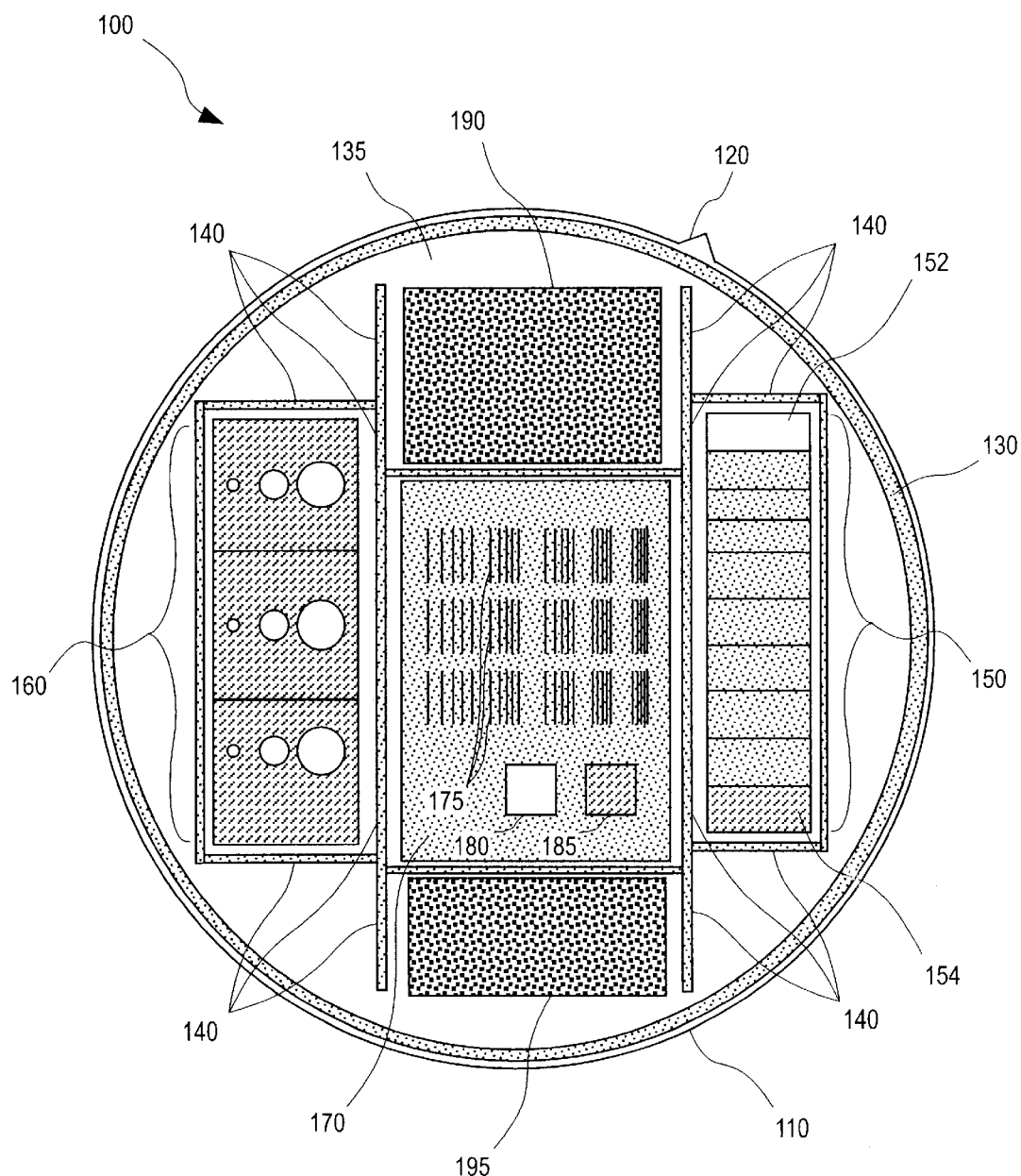
FIG. 1 illustrates a preferred embodiment of an x-ray phantom according to the present invention.

FIG. 1 illustrates a preferred embodiment of an x-ray phantom 100 of the present invention. The phantom 100 includes a base 110, a positioning tab 120, a perimeter ring 130, an open area 135, line segments 140, a step intensity sub-phantom 150, a contrast detail sub-phantom 160, a resolution sub-phantom 170, an upper mesh 190, and a lower mesh 195. The resolution sub-phantom 170 includes resolution patterns 175, a high intensity contrast region 180 and a low intensity contrast region 185.

The positioning tab 120 extends radially from the base 110. The positioning tab is used to assure that the phantom 100 is positioned correctly inside a phantom carrier. The positioning tab 120 minimizes rotational motion of the phantom 100 and also prevents the phantom 100 from being placed in a carrier incorrectly, for example upside down. Additional positioning tabs may be added to the x-ray phantom to further minimize the motion of the phantom.

The perimeter ring 130, line segments 140, step intensity sub-phantom 150, contrast detail sub-phantom 160, and resolution sub-phantom 180, and upper and lower meshes 190–195 are affixed to the top of the base 110. The perimeter ring 130 runs along the perimeter of the base 110. The line segments 140 separate the step intensity sub-phantom 150, contrast detail sub-phantom 160, resolution sub-phantom 170, and upper and lower meshes from each other and from the open area 135.

In operation, the phantom 100 may be inserted into an x-ray system (not shown). In an x-ray system, x-rays are emitted by an emitter, pass through the phantom 100, and are received by a receiver. The differing sub-phantoms comprising the phantom 100 attenuate x-rays incident on the sub-phantoms by differing amounts and may be influenced by the composition or structure of the sub-phantom, for example. The x-ray attenuation provided by the sub-phantoms results in spatially varying x-ray intensity at the receiver. The spatially varying intensities may be received at the receiver and displayed and analyzed to determine the performance parameters of the x-ray system. Each sub-phantom may measure a different performance parameter or set of performance parameters of the x-ray system.

The perimeter ring 130 and the line segments 140 are preferably composed of a metallic layer such as lead, for example, that blocks much of the x-ray transmission through the phantom 100. Because the perimeter ring 130 and the line segments 140 block a comparatively large amount of the x-ray transmission through the phantom, they are easily detectable when displayed and analyzed. The perimeter ring 130 and line segments 140 thus provide easily seen "landmarks." These landmarks aid in determining the orientation and positioning of the phantom 100. For example, the perimeter ring 130 may be used to define the perimeter of the phantom 100 in an x-ray image to aid in recognition and interpretation of phantom data. Additionally, the line segments 140 may be used to separate the sub-phantoms 150–170 and also to define the perimeters of each sub-phantom.

Figure 10:
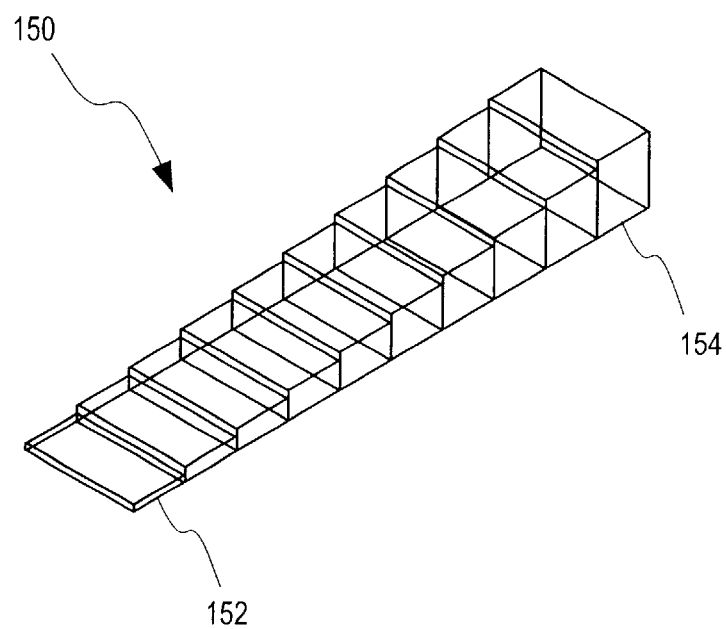
FIG. 10 illustrates a preferred embodiment of the step intensity sub-phantom according to the present invention.

FIG. 10 illustrates a preferred embodiment of the step intensity sub-phantom 150 according to the present invention. The step intensity sub-phantom 150 is preferably composed of a metallic layer such as copper, for example. The step intensity sub-phantom 150 preferably includes ten regions, each region composed of a differing thickness of the copper layer. The thickness of the copper layer in each region ranges from a thinnest region 152 to a thickest region 154. Because the intensity of the x-rays penetrating a given region is inversely proportional to the thickness of the region, each region provides a level or "step" in intensity from greatest intensity to least intensity. Preferably, each of the regions of the step intensity sub-phantom 150 are approximately 20 mm across by 7.5 mm high and range linearly from about 0.25 mm to 2.5 mm in thickness. The step intensity sub-phantom 150 may be used to determine the dynamic range and the linearity of the x-ray system. Although the preferred embodiment of the step intensity sub-phantom 150 is comprised of ten regions, a greater or lesser number of regions of varying sizes and thicknesses may also be used.

Figure 11:
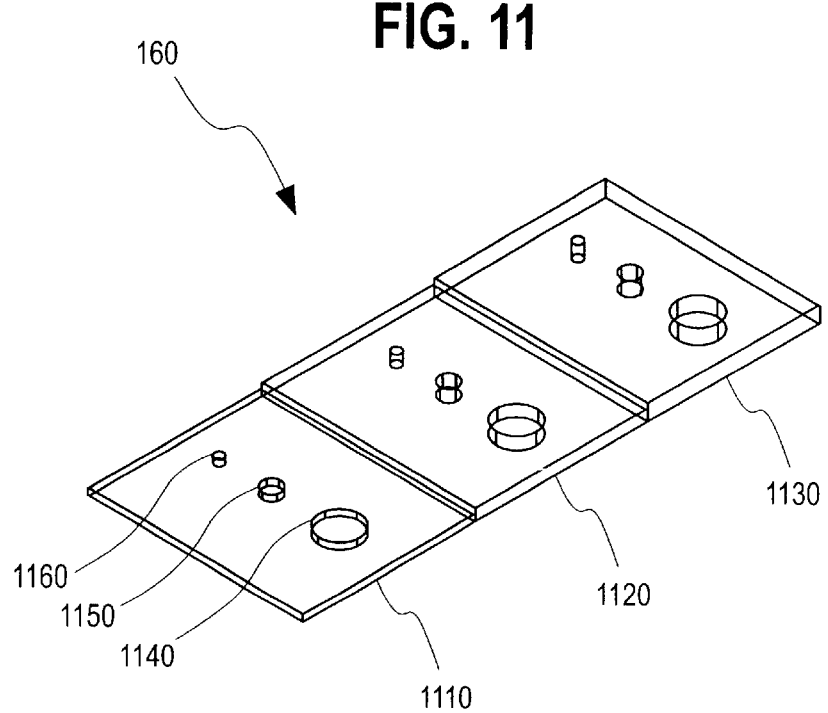
FIG. 11 illustrates a preferred embodiment of the contrast detail sub-phantom according to the present invention.

FIG. 11 illustrates a preferred embodiment of the contrast detail sub-phantom 160 according to the present invention. The contrast detail sub-phantom 160 is preferably composed of a metallic layer such as aluminum, for example. The contrast-detail sub-phantom 160 preferably includes three regions 1110–1130, each region composed of a differing thickness of the aluminum layer. The thickness of the aluminum ranges from a thinnest layer 1110 to a thickest layer 1130. Each region preferably contains three apertures 1140–1160 of approximately 7.6 mm, 3.8 mm. and 1.9 mm in diameter. Preferably, each of the regions 1110–1130 of the contrast detail sub-phantom 160 are approximately 30 mm across by 20 mm high with thicknesses of 1 mm, 2 mm, and 3 mm. The contrast detail sub-phantom 160 may be used to determine the relative contrast and contrast-to-noise ratio of the x-ray system. Although the preferred embodiment of the contrast detail sub-phantom 160 is comprised of three regions 1110-1130 with three apertures 1140–1160 per region, a greater or lesser number of regions and apertures per region may also be used.

Figure 12:
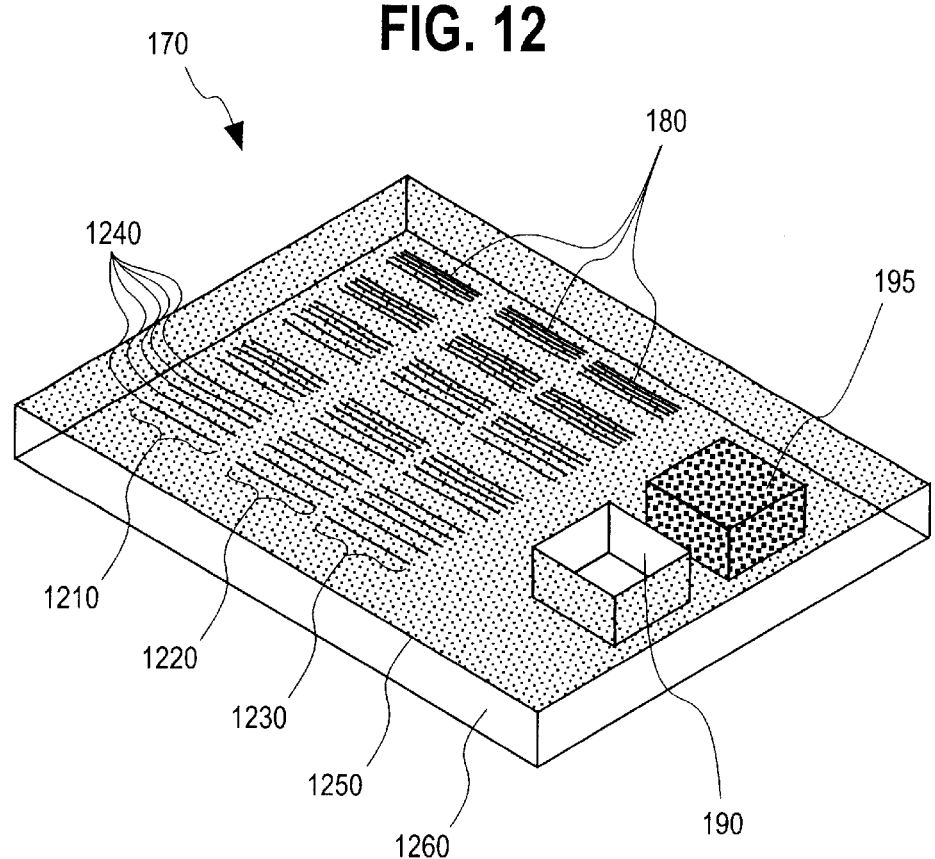
FIG. 12 illustrates a preferred embodiment of the resolution sub-phantom according to the present invention.

FIG. 12 illustrates a preferred embodiment of the resolution sub-phantom 170 according to the present invention. The resolution sub-phantom 170 is preferably composed of a thin metallic layer 1250 such as lead foil, for example on top of a base 1260 such as plastic, for example. The resolution sub-phantom 170 and the metallic layer 1250 have a uniform thickness throughout. The resolution sub-phantom 170 preferably includes fifteen resolution patterns 180 arranged in three rows 1210–1230, each row 1210–1230 including five resolution patterns 180. Each resolution pattern 180 is preferably formed by five slit-like apertures 1240 extending through the metallic layer 1250. In each resolution pattern 180, the width of the five slit-like apertures 1240 as well as the spacing between apertures 1240 may be varied. The resolution sub-phantom 170 may be used to determine the Modulation Transfer Function (MTF) of the x-ray system.

Although the preferred embodiment of the resolution sub-phantom 170 includes fifteen resolution patterns 180 arranged in three rows 1210–1230 of five resolution patterns per row 1210–1230, a greater or lesser number of resolution patterns may also be used. Additionally, the configuration of the resolution patterns 180 into rows 1210–1230 or other structures may be altered. Additionally, the widths and lengths of the apertures 1240 of the resolution patterns 180 may be varied.

The high intensity contrast region 190 is preferably comprised of a an aperture in the metallic layer 1250 and the base 1260. The low intensity contrast region 195 is preferably comprised of a thick metallic tag such as a lead block. The high intensity contrast region 190 and the low intensity contrast region 195 provide high and low contrast regions respectively, and may be used for image normalization.

Figure 13:
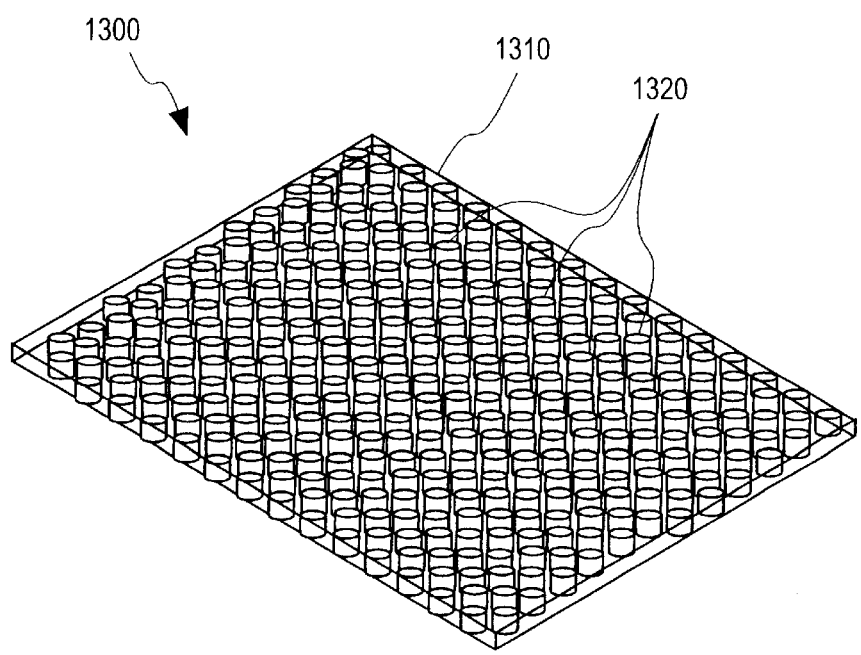
FIG. 13 illustrates a preferred embodiment of a mesh area similar to the upper mesh and lower mesh according to the present invention.

FIG. 13 illustrates a preferred embodiment of a mesh area 1300 similar to the upper mesh 190 and lower mesh 195 according to the present invention. The mesh area 1300 is preferably a metallic mesh such as a steel mesh. The mesh area 1300 includes a metallic strip 1310 having a number of regularly spaced apertures 1320. The upper mesh 190 and lower mesh 195 may be used to determine the resolution non-uniformity of the x-ray system. The resolution non-uniformity of the x-ray system may be determined across a single mesh or may be determined across multiple meshes and then compared. Comparison of the resolution non-uniformity among multiple meshes may allow a determination of resolution non-uniformity across a greater area and thus may be more accurate of the resolution non-uniformity of an x-ray system as a whole. Thus, although the preferred embodiment of the phantom 100 includes two meshes to provide increased accuracy in determining system non-uniformity, a single mesh may be used. Additionally, more than two meshes may be used to yield an even more accurate indication of system non-uniformity. The sizes, thicknesses, and spacing of the apertures of the meshes may also be varied.

Figure 2:
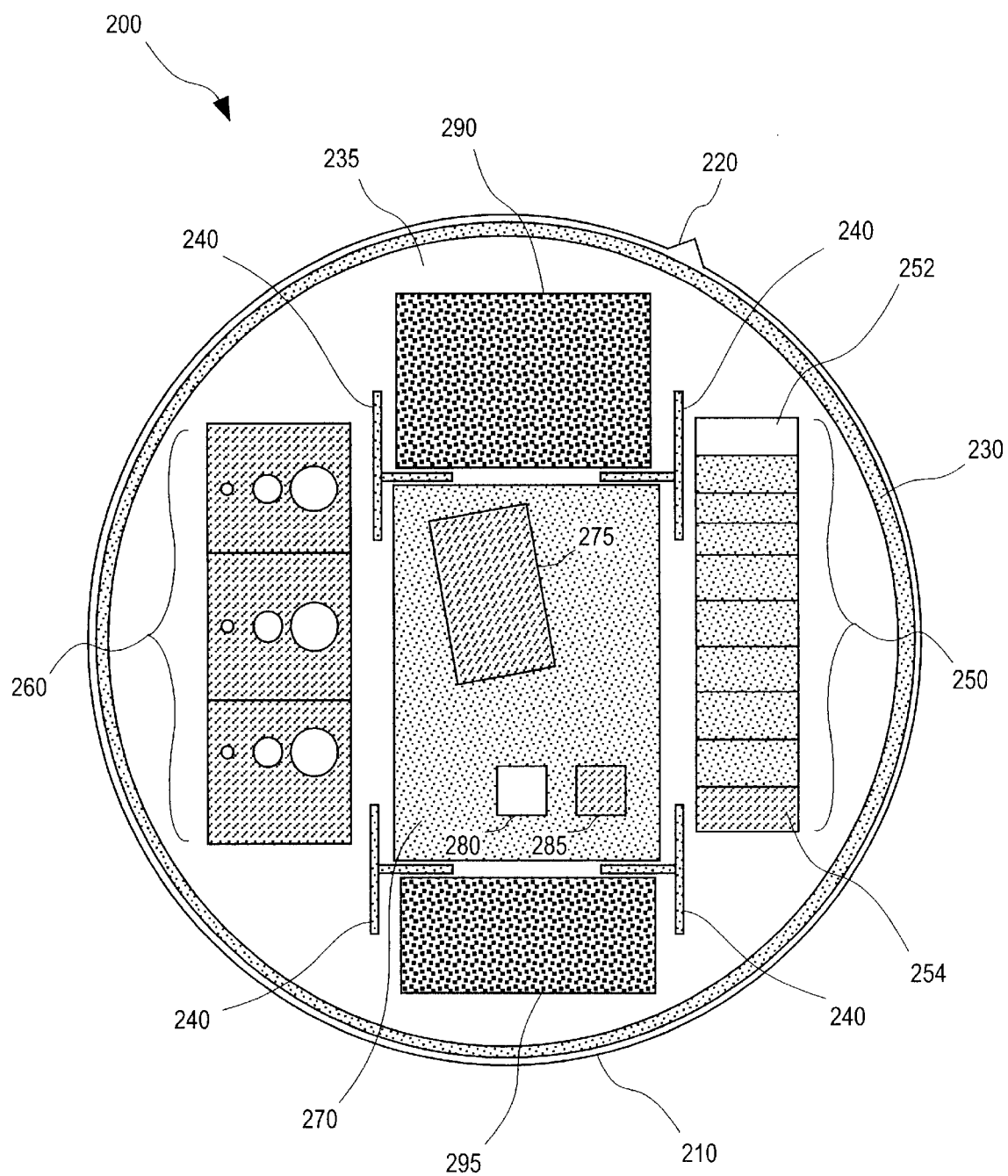
FIG. 2 illustrates an alternative preferred embodiment of an x-ray phantom with a coupon sub-phantom according to the present invention.

FIG. 2 illustrates an alternative preferred embodiment of a x-ray phantom 200 with a coupon sub-phantom 270 of the present invention. The coupon phantom 200 includes a base 210, a positioning tab 220, a perimeter ring 230, an open area 235, a step intensity sub-phantom 250, a contrast detail sub-phantom 260, and upper and lower meshes 290–295 similar to the phantom 100 of FIG. 1. However, the coupon phantom 200 includes fiducials 240 instead of the line segments 140 of the phantom 100 of FIG. 1. Additionally, the coupon phantom 200 includes a coupon sub-phantom 270 instead of the resolution sub-phantom 170 of FIG. 1.

Figure 14:
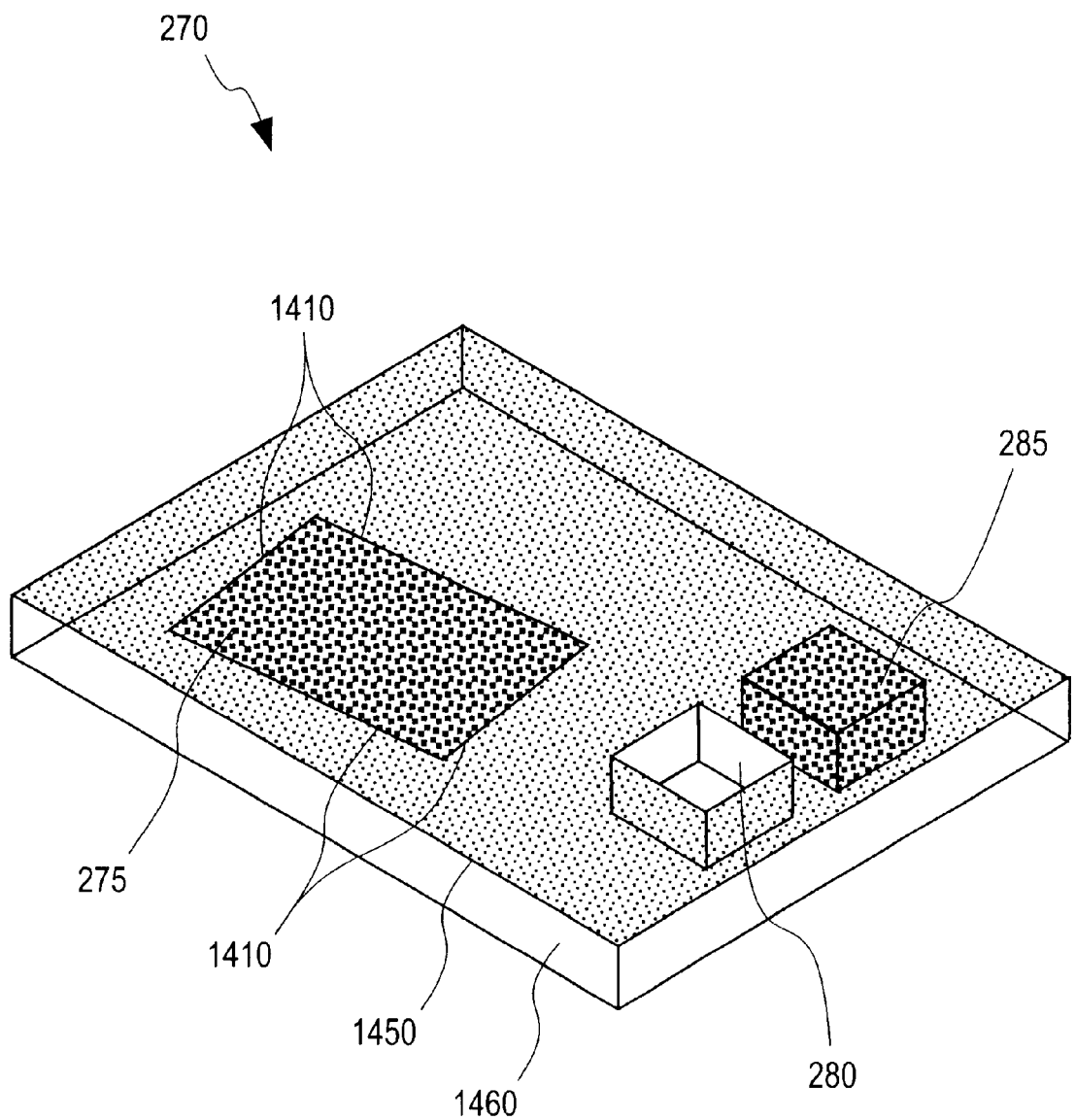
FIG. 14 illustrates a preferred embodiment of the coupon sub-phantom according to the present invention.

FIG. 14 illustrates a preferred embodiment of the coupon sub-phantom 270 according to the present invention. The coupon sub-phantom 270 includes a coupon 275 in addition to a thin metallic layer 1450 such as lead foil, for example, on top of a base 1460 such as plastic, for example, a high intensity contrast region 280 and a low intensity contrast region 285 similar to the phantom 100 of FIG. 1. The coupon sub-phantom 270 and the metallic layer 1450 have a uniform thickness throughout. The coupon 275 is preferably composed of a metallic sheet such as a tungsten sheet, for example. Similar to the resolution patterns 180 of the resolution sub-phantom 170 of FIG. 1, the coupon 275 may be used to determine Modulation Transfer Function (MTF) of the x-ray system. Although the preferred embodiment of the coupon phantom 200 includes one coupon 275, a greater number of coupons of varying sizes and thicknesses may also be used.

The coupon 275 has coupon edges 1410. The MTF of the X-ray system may be determined by comparing the transitions at the coupon edges 1410 with respect to position.

Examining the resolution patterns 180 of the resolution sub phantom 170 of FIG. 1, the resolution patterns 180 vary only in horizontal aspect, no variation is seen vertically. Thus, the resolution patterns 180 may only calculate the horizontal MTF of the system and not the vertical MTF of the system.

However, in the coupon sub-phantom 270, the coupon edges 1410 have been rotated 5 degrees with respect to the coupon sub-phantom 270. The coupon edges 1410 thus provides both vertical and horizontal variation. The horizontal and vertical variation allow the computation of both the horizontal MTF and vertical MTF of the x-ray system. The amount of rotation of the coupon 275 is related to the resolution of the x-ray system in terms of pixel size as well as the size of the coupon 275. Additionally, rotating the coupon 275 assists in the measurement of the MTF because the edges of the coupon 275 do not align with a pixel column. For many commercially available systems, a rotation of approximately 5 degrees may be the most desired rotation although other rotations may also provide accurate MTF determination.

The fiducials 240 of the coupon phantom 200 of FIG. 2 are preferably composed of a metal such as lead for example. The fiducials 240 are generally similar in operation to the line segments 140 of the phantom 100 of FIG. 1. That is, the fiducials 240 are easily seen "landmarks" in an x-ray image of the phantom. The fiducials 240 may thus aid in determining the orientation and positioning of the coupon phantom 200 as well as aid in separating and locating the various sub-phantoms.

The shape, size, and positioning of the fiducials 240 may also be used to distinguish between phantoms. For example, a phantom measuring parameters A and B may have a different shape, size and orientation of fiducials than a phantom measuring parameters B and C. For example, the phantom 100 of FIG. 1 may be distinguished from the coupon phantom 200 of FIG. 2 because the fiducials 240 differ from the line segments 140. Distinguishing between phantoms on the basis of fiducials is useful because the fiducials are made of lead and thus are easily seen in x-ray images.

In operation, phantoms such as the phantom 100 of FIG. 1 and the phantom 200 of FIG. 2 are positioned in an x-ray system (not shown) including an x-ray emitter and an x-ray receiver, as described above. The emitter emits x-rays which pass through the phantom to the receiver. The x-rays passing through the phantom are attenuated. The amount of attenuation experienced by the x-rays is due to the phantom structure that the x-ray passes through to reach the receiver. Because the phantom structure varies spatially, the x-ray attenuation provided by the phantom results in spatially varying x-ray intensity at the receiver. The surface of the receiver may be spatially partitioned into a grid and the x-ray intensity incident upon each element of the grid may be digitized to form an image representative of the received x-ray intensity at each grid area. Each grid area may correspond to a pixel in a resultant x-ray image.

An x-ray image is typically embodied as a gray scale image. In a gray scale image, each pixel has a gray value ranging from a lowest level (represented as white in an x-ray image) to a highest level (represented as black in an x-ray image). The x-ray image is commonly an 8-bit (256 level) to 16-bit (16,384 level) image. Although the common 8-bit digitization level is used in the following examples, other digitization levels are possible and the present invention may be applied regardless of digitization level. Additionally, any digitization level may be converted to an 8-bit digitization level, for example by dividing the digitization of each pixel in the image by $2^{n-8}$ where n is the alternate digitization level.

Figure 3:
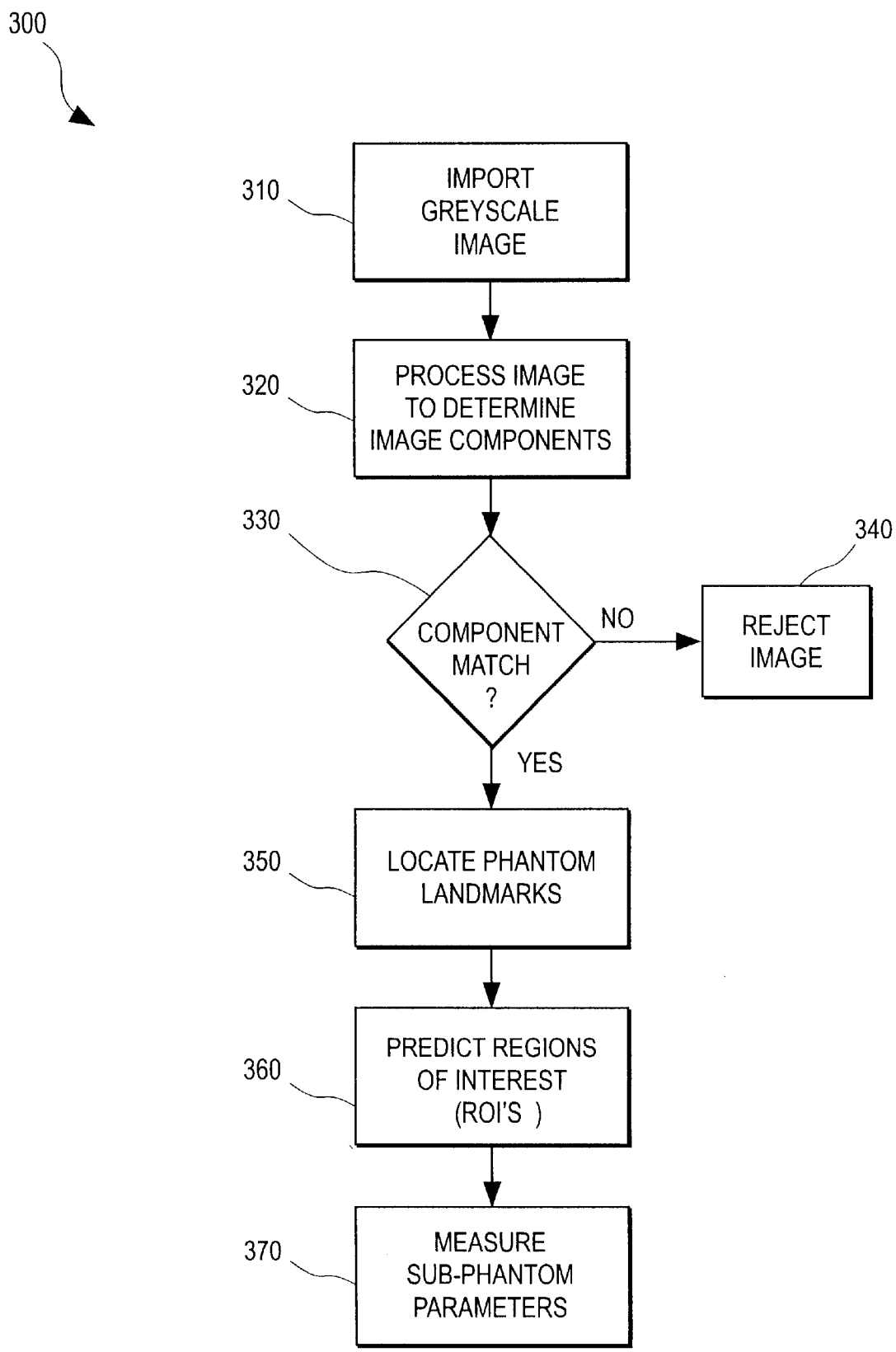
FIG. 3 illustrates a flowchart of a preferred embodiment of an automated phantom evaluation system according to the present invention.

FIG. 3 illustrates a flowchart 300 of a preferred embodiment of an automated phantom evaluation system according to the present invention. The automated phantom evaluation system first imports a grayscale x-ray image at step 310. The grayscale image is then processed to determine the image components at step 320. The image components may include the images of a perimeter ring 130, 230 or the coupon 275 of the phantom 200 of FIG. 2. Next, the components of the image are compared with the predetermined, expected image components at step 330. The structure of the phantoms 100, 200 of FIG. 1 and FIG. 2 is known, as well as the x-ray image that the structure of the phantoms generates. Accordingly, the image components of the imported image may be compared to expected image components for identification or quality, for example. If the components of the imported image do not match the expected components, the imported image is rejected at step 340 and no further processing occurs. If the components of the imported image match the expected components (within a tolerance), then the imported image is accepted and processing continues. At step 350, landmarks such as the line segments 140 of the phantom 100 of FIG. 1 and the fiducials 240 of the phantom 200 of FIG. 2 are located. The landmarks provide localization of the sub-phantoms such as the coupon sub phantom 275. Next, at step 360, the Regions Of Interest (ROIs) for each sub-phantom are calculated. The ROIs are determined using the landmarks and are the areas within the sub-phantoms in which the measurement of the various x-ray system parameters occurs. Finally, at step 370, the x-ray system parameters are measured within each sub-phantom. The various steps of the flowchart 300 are discussed in greater detail below.

Figure 4:
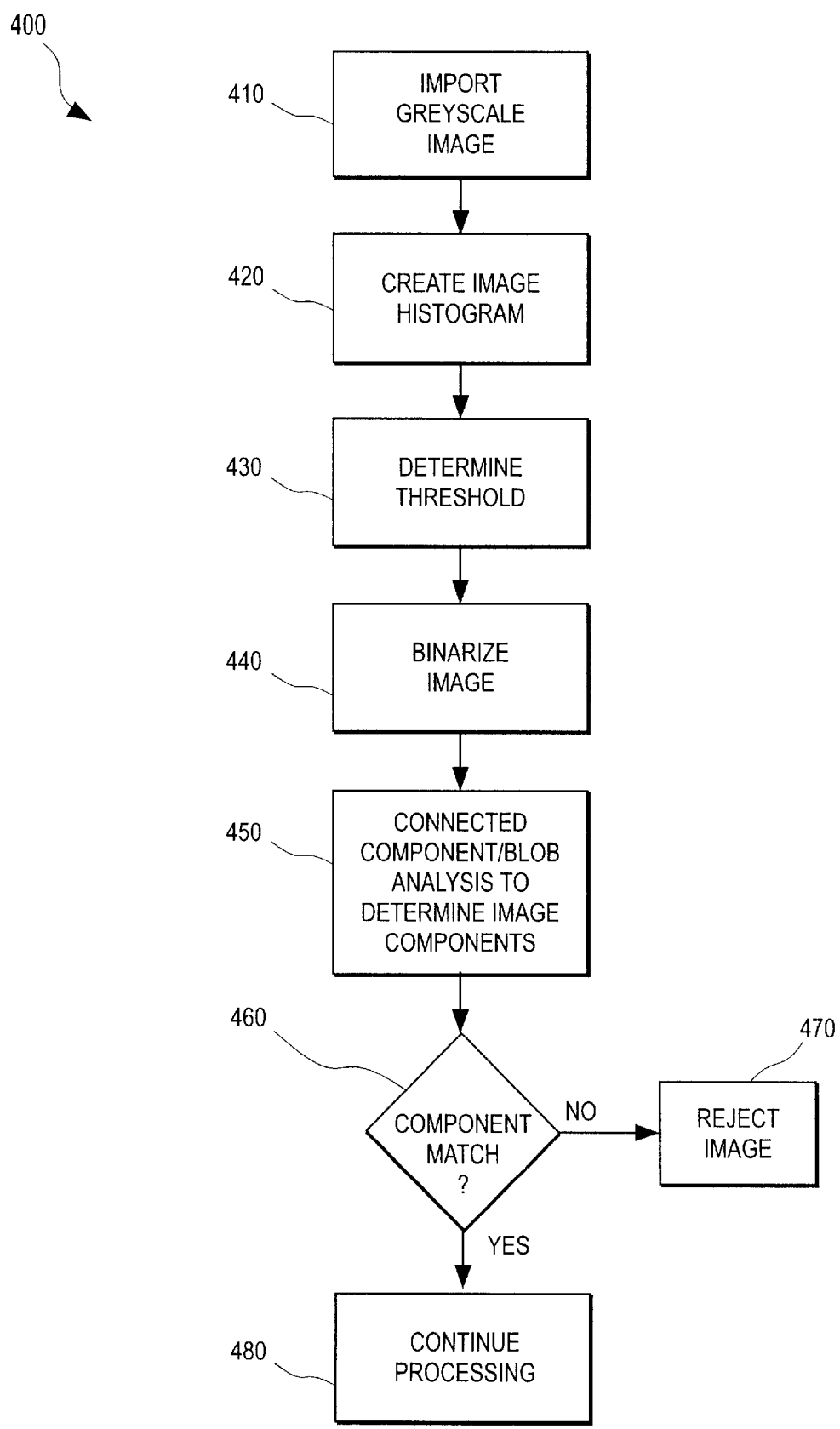
FIG. 4 illustrates a flowchart of a preferred embodiment for image processing to determine image components according to the present invention.

FIG. 4 illustrates a flowchart 400 of a preferred embodiment of image processing to determine image components according to the present invention and step 310–330 of the flowchart of FIG. 3. First, at step 410, the grayscale image is imported into the automated phantom evaluation system. Next, at step 420 an image histogram of the imported grayscale image is created. The image histogram is formed by determining the number of pixels in the image having each pixel value. For example, in an 8-bit, 256 level digitization, the number pf pixels having a pixel value corresponding to the first level is determined, then the number of pixels having a pixel value corresponding to the second level is determined, and so forth for all 256 levels. The image histogram may also be expressed as a plot of the pixel values versus the pixel population.

FIG. 5 illustrates an exemplary image histogram 500 according to the preferred embodiment of the present invention. The horizontal axis 510 of the histogram 500 has an axis point for each of the 256 pixel values of the grayscale image. The vertical axis 520 has an axis point for each of the N possible population values of the pixel values of the grayscale image. An example is illustrated for the case where two pixels within the grayscale image have a pixel value of zero while one of the pixels within the grayscale image has a pixel value of one.

The histogram 500 also includes a curve 530 that is generally representative of an expected 8-bit (256 level) digitized grayscale image of an imported image components in a phantom such as the phantom 100 of FIG. 1 or the phantom 200 of FIG. 2. Any image histogram is dependent upon the composition of the imported image components of the phantom. For example, a phantom generating an image with large dark areas may have a histogram with large populations at higher pixel value levels while an image with large light areas may have a histogram with large populations at lower pixel value levels. The curve 530 of the histogram 500 indicates the imported grayscale image has both large light and dark areas with relatively lesser areas of middle contrast. The dark areas in the imported image may correspond to such areas as the perimeter ring 130, line segments 140, the solid areas of the contrast detail sub-phantom 160 and the resolution sub-phantom 170 of the phantom 100 of FIG. 1, for example. The light areas in the image may correspond to the open area 135. Because the image for the phantom 100 of FIG. 1 has large light and dark areas, the histogram of the image has two distinct peaks centered around the average values for the light areas 540 and the average value for the dark areas 550. In the images of the phantom 100 of FIG. 1 and the phantom 200 of FIG. 2, the features of interest, such as landmarks, represent dark areas in the image and are centered around the second peak. Because the images of the phantoms 100, 200 contain large dark areas, the peak corresponding to dark areas is relatively larger and may be more easily located.

The image histogram 500 is then analyzed to determine a threshold value according to step 440 of the flowchart 400 of FIG. 4. In the image of the phantoms 100, 200, the threshold is selected to eliminate the pixel values corresponding to light areas and accept the pixel value levels corresponding to dark areas. The pixel values levels corresponding to dark areas are valuable because the landmarks are dark areas. Locating the pixels corresponding to dark areas locates the landmarks. The actual threshold is preferably the mid-point 560 between the peaks of the histogram, but any value allowing differentiation between light and dark regions may be employed. The pixel value corresponding to the local minima 570 may also be a useful threshold. The threshold is preferably selected individually for each image to eliminate variance due to positioning and phantom structure.

Next, at step 440, the histogram of the imported grayscale image is computed. The histogram is assumed to be bimodal and is analyzed to automatically determine an appropriate grayscale threshold. This threshold is then used to binarize the image. That is, each pixel is assigned one of two binary levels based on whether the pixel value for that pixel is greater or not greater than the threshold pixel value. For example, if the threshold pixel value is 145, then a pixel with a pixel value of 200 (corresponding to a pixel lighter than the threshold) may be set to one while a pixel with a pixel value of 100 (corresponding to a pixel darker than the threshold) may be set to zero.

Next, at step 450, connected component analysis is employed to determine the components of the imported grayscale image. In connected component analysis, the binarized image is iteratively scanned to identify "blobs" or connected dark pixels. First, each dark pixel is analyzed to determine if a neighboring pixel is also dark, if so then the dark pixel and it's neighbor form a "blob". The next iteration determines if any of the pixels neighboring the blob are also dark. If so then the neighboring pixels are included as part of the blob. The iterations proceed until all blobs in the image have been identified and no blob neighbors another blob. Because the dark pixels may correspond to the components of the phantoms 100, 200, connected component analysis is a convenient system for identifying the spatial extent of the components. For example, the blobs may correspond to physical components in the phantom 200 of FIG. 2 such as the coupon 275, fiducials 240, or perimeter ring 230.

Once all the blobs have been determined, the attributes of each blob, including blob area and blob density, for example, are determined. To determine the attributes of each blob, first a "bounding box" is constructed around each blob. The bounding box is a rectangle comprised of straight horizontal and vertical lines positioned in each direction at the maximum spatial extent of each blob.

Figure 6A:
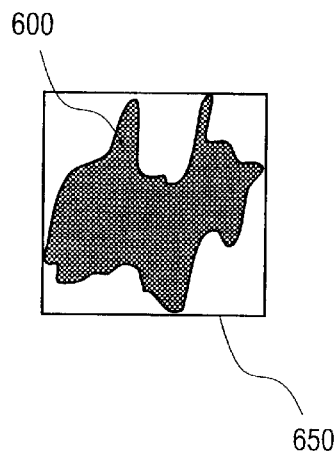
FIGS. 6a–d illustrate exemplary blobs and accompanying bounding boxes according to a preferred embodiment of the present invention.
Figure 6B:
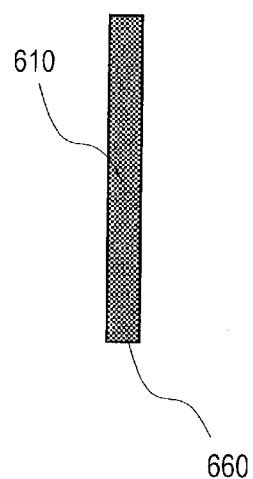
Figure 6C:
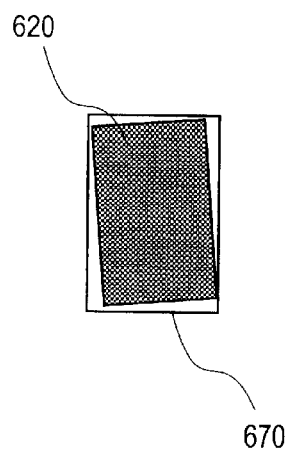
Figure 6D:
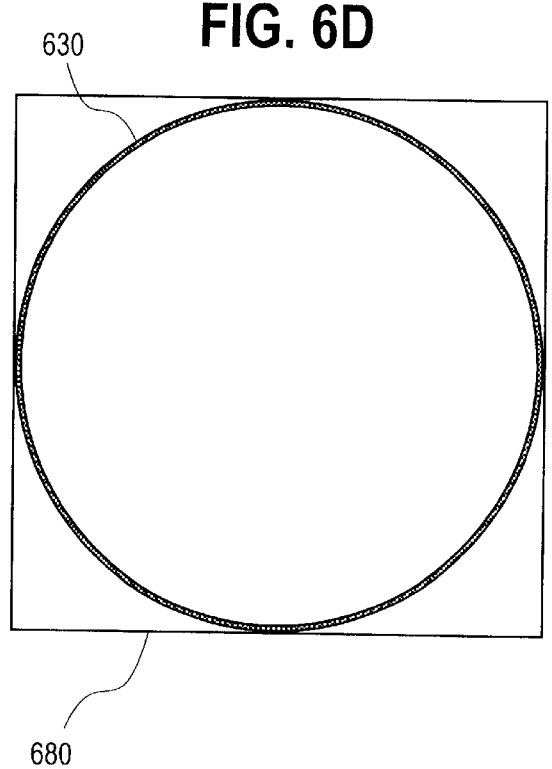

FIGS. 6a–d illustrate some exemplary blobs 600–630 and accompanying bounding boxes 650–680 according to the present invention. FIG. 6a illustrates a blob 600 and its accompanying bounding box 650. The bounding box is comprised of horizontal and vertical lines positioned at the edges of the blob. Blob area is the area inside the bounding box. Blob density is the proportion of dark pixels to the total number of pixels in the blob. Alternatively, blob density is the proportion of dark pixels compared to the blob area. The blob 600 of FIG. 6a has a relatively low blob density of around 50%. FIG. 6b illustrates a blob 610 and its accompanying bounding box 660. Because the blob is aligned vertically and horizontally, the density of the blob is approximately maximal. FIG. 6c illustrates a blob 620 and its accompanying bounding box 670. The blob 620 is solid and aligned nearly vertically. The blob density of the blob 620 is high. The blob 620 is generally similar to the blob generated by the coupon 275 of the phantom 200 of FIG. 2. FIG. 6d illustrates a blob 630 and its accompanying bounding box 680. The blob density of the blob 630 is low. The blob 630 is generally similar to the blob generated by the perimeter ring 130, 230 of the phantoms 100, 200 of FIGS. 1 and 2. The blob 630 also has a blob area larger than any other blob.

Each of the components of the phantoms 100, 200 of FIGS. 1 and 2, including the perimeter ring 130, 230, line segments 140, and fiducials 240, for example, has a known blob area and density when image processed. Thus, the blob area and density for each blob in the imported image may be compared to the expected area and density of the of phantom components. For example, the area and density of each of the blobs in the imported image is compared with the area and density of the perimeter ring to determine which blob in the imported image corresponds to the perimeter ring. In the same way, each of the blobs in the imported image is compared to the attributes of each of the expected components.

Next at, step 460, it is determined if all of the expected components are identified in the imported image, that is, if the blobs of the imported image match the area and density of the expected blobs, within a tolerance. If not all of the blobs match, then the image is rejected at step 470 and no further processing takes place. If all of the blobs match, then processing of the imported image continues. The tolerance in matching the blobs is preferably employed so that the correspondence between blob area and density and expected area and density need not be exact. Blobs not conforming to the expected blob area and density for any of the image components are discarded. The selected threshold level impacts the size and shape of the blobs. For example, if the threshold is set too low, noise my be included in the connected component analysis. The included noise may serve to connect blobs such as the perimeter ring and fiducials, for example, and render image recognition difficult.

FIG. 7 illustrates a flowchart 700 of a preferred embodiment of locating phantom landmarks according to the present invention and step 350 of the flowchart of FIG. 3. First, at step 710, the midpoint and radius of the perimeter ring is determined. Once the blob corresponding to the perimeter ring has been determined, a circle fitting system may be used to determine the center and radii of the perimeter ring. The circle fitting system preferably uses the least squares method to iteratively determine the midpoint and radius of the perimeter ring. First, the circle fitting system identifies the location of each pixel in the blob corresponding to the perimeter ring. Next, an initial estimate of the midpoint is selected and the radius from the midpoint to each pixel on the ring is determined. Then, the average and variance of the radii are then determined. If the variance is high, a new midpoint estimate is selected and another iteration occurs.

Next, at step 720, the variance in the midpoint estimate is compared to a tolerance. If the variance is within the tolerance, then the estimated midpoint is accepted as the midpoint of the perimeter ring and processing of the imported image continues. If the variance remains large after many iterations, then a circular structure has not been found and the phantom is rejected at step 730.

Once the midpoint and radius of the blob corresponding to the perimeter ring have been determined, the next step is to distinguish between the mesh phantom 100 of FIG. 1 and the coupon phantom 200 of FIG. 2 at step 740. The type of phantom (either phantom 100 or phantom 200) may either be entered by a user or automatically identified. The type of phantom may be auto-identified by first comparing the blob attributes in the imported phantom with the expected blob attributes of the mesh phantom 100. If the blob attributes do not match, then the blob attributes of the imported phantom are compared with the blob attributes of the coupon phantom 200. If the blob attributes do not match either phantom, then the phantom is rejected at step 745.

If the imported image is identified at the phantom 100 of FIG. 1, then the line segments are located, beginning with the vertical line segments in the imported image at step 750. Although the location of the perimeter ring has been determined at step 710, the location of the other phantom components is not necessarily known due to errors in positioning and rotation, for example. Detecting the location of the line segments 140 assists in maintaining the accuracy of positioning within the image and aids in making repeatable measurements.

Figure 8:
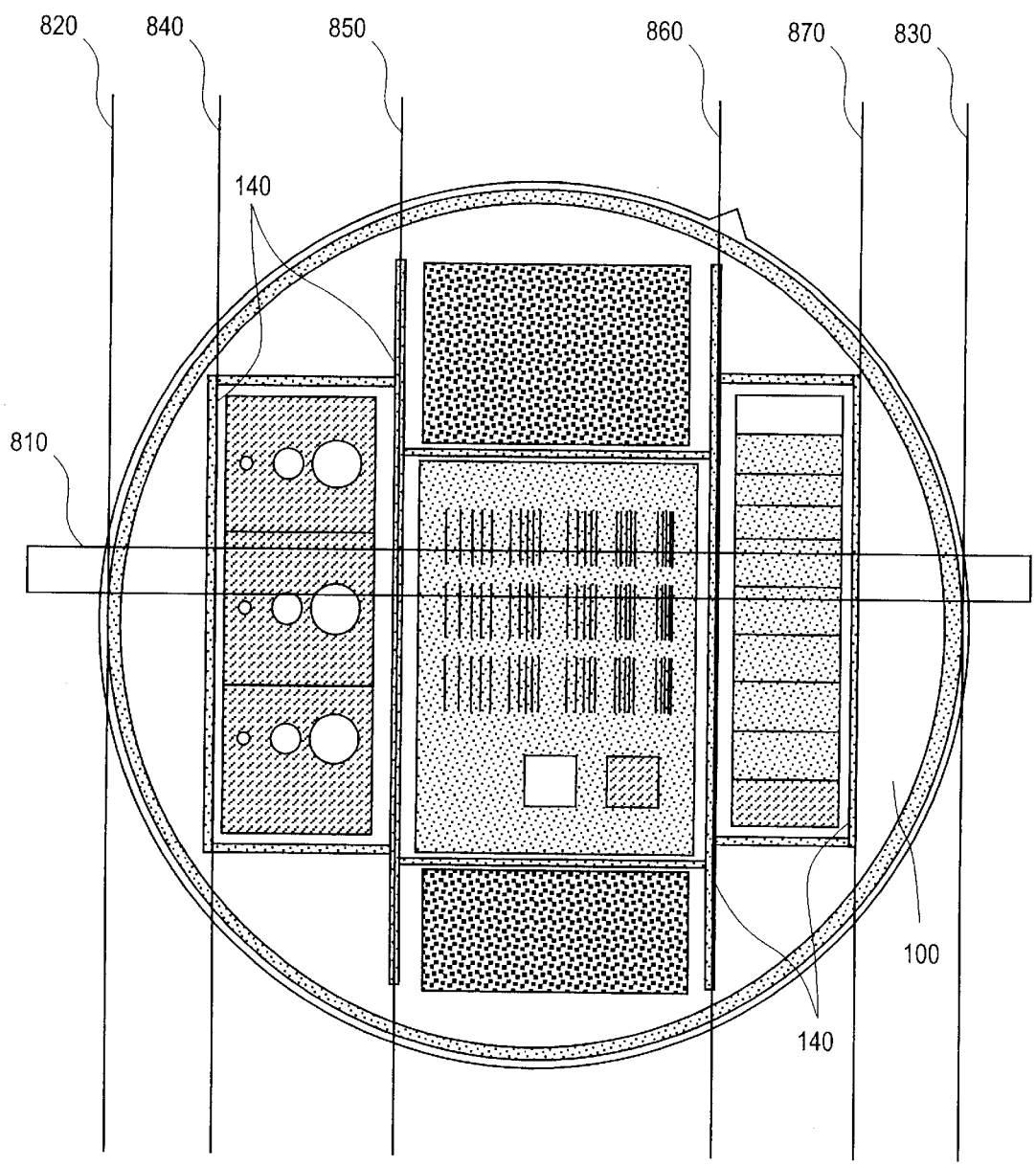
FIG. 8 illustrates the determination of the locations of the vertical line segments of the phantom of FIG. 1 according to a preferred embodiment of the present invention.

FIG. 8 illustrates the determination of the locations of the vertical line segments 140 of the phantom 100 of FIG. 1. FIG. 8 includes a horizontal search area 810, a left perimeter ring edge 820, a right perimeter ring edge 830, a left contrast detail sub-phantom edge 840, a right contrast detail sub-phantom edge 850, a left step intensity sub-phantom edge 860, and a right step intensity sub-phantom edge 870. At first, the only known elements of FIG. 8 are the left perimeter ring edge 820 and right perimeter ring edge 830 which are the vertical edges of the boundary box surrounding the blob representing the perimeter ring. The search area 810 is then positioned horizontally across the edges 820, 830. The search area 810 is several pixels high and extends across the phantom 100.

The pixel values of each pixel in each row in the search area 810 are examined. Within each row, the pixel positions corresponding to large differences in pixel value between adjacent pixels are identified. The large differences in pixel value correspond to the transitions between the lead line segments 140 and the open areas 135. By averaging the pixel positions in each row corresponding to the transitions over all the rows in the search area, the location of the vertical line segments may be accurately determined. Thus, the locations of the left contrast detail sub-phantom edge 840, right contrast detail sub-phantom edge 850, left step intensity sub-phantom edge 860, and right step intensity sub-phantom edge 870 are determined. Although some change in pixel value may be experienced as a row in the search area passes over a sub-phantom or the resolution patterns 175 of the resolution sub-phantom, the changes in pixel value are not as large as the transitions for the vertical lead lines.

Figure 9:
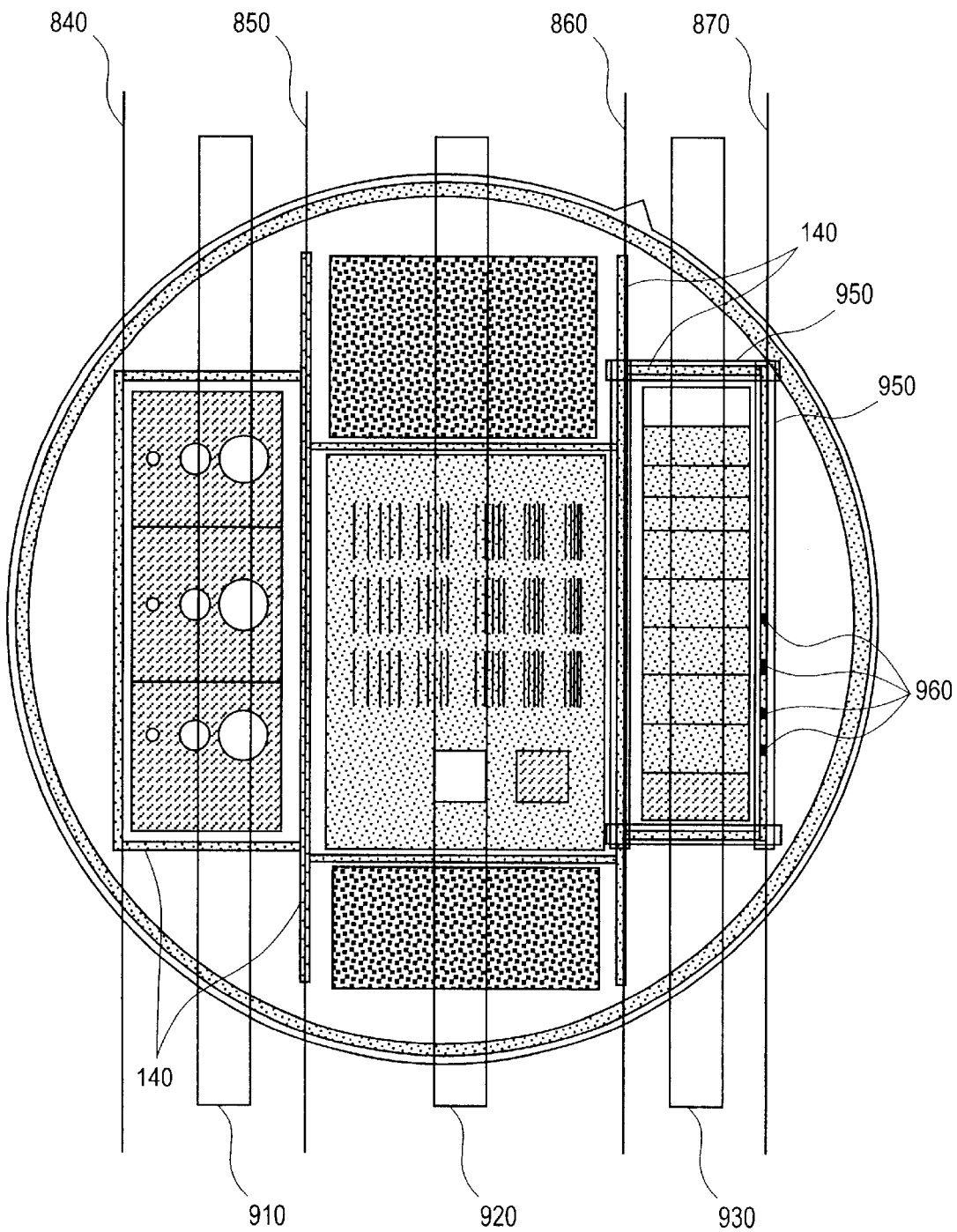
FIG. 9 illustrates the determination of the locations of the horizontal line segments of the phantom of FIG. 1 according to a preferred embodiment of the present invention.

Next, at step 760 of the flowchart 700 of FIG. 7, the horizontal line segments are located. FIG. 9 illustrates the determination of the locations of the horizontal line segments 140 of the phantom 100 of FIG. 1. FIG. 9 includes three vertical search areas a left search area 910, a center search area 920, and a right search area 930. The search areas are positioned between the previously determined left contrast detail sub-phantom edge 840, right contrast detail sub-phantom edge 850, left step intensity sub-phantom edge 860, and right step intensity sub-phantom edge 870 as shown. The vertical search areas 910–930 function generally similarly to the horizontal search area 810 of FIG. 8. That is, within each column, the pixel location of large transitions is identified. The pixel locations of the transitions are then averages across the columns to determine the horizontal line segments 140.

Next, at step 770, equally spaced points on each line segment are detected and tracked. The location of the vertical and horizontal line segments was previously determined within a small search area. The search areas for the vertical and horizontal line segments are now extended and tracked over a search area covering their entire length. FIG. 9 shows the four search areas 950 corresponding to the vertical and horizontal line segments surrounding the step intensity sub-phantom. The search areas are used to track the center of their respective line segment. Points are placed at equal spacings at the pixels corresponding to the center of the line segments.

The coordinates of equally spaced points in the image may be used as registration points. These registration points and their corresponding points on the stored physical model of the phantom may be used to obtain a polynomial warping or transformation. A separate polynomial transformation may be obtained for each component or sub-phantom based on line segments that surround it. The polynomial warping may provide an accurate prediction of the Regions of Interest (ROIs) in each sub-phantom. Polynomial warping is particularly effective on imaging systems that are susceptible to geometric distortion, resulting in vertical or horizontal lines that are not necessarily straight. The polynomial warping may be used to generate a "best fit" among the registration points which may then be mapped to the stored physical model of the phantom.

Next, at step 780, the aspect ratios of the phantom components are verified. Because the locations of the vertical and horizontal line segments are known and the spatial relationship of the vertical and horizontal lines on the phantom is also known, the aspect ratio of the tracked vertical and horizontal line segments may be compared with the aspect ratio of the physical phantom. If the aspect ratio of the imported image does not agree with the expected aspect ratio within a tolerance, then the phantom is rejected at step 785 and no further processing occurs. If the aspect ratio of the imported image agrees with the expected aspect ratio, then image processing proceeds to step 790.

At step 790, the ROIs of the phantom are predicted. The ROIs are the points within the image that x-ray system parameter measurements take place. The ROIs are predicted based on the locations of the vertical and horizontal line segments. If the vertical and horizontal line segments are not straight, then polynomial warping is employed to develop a working estimate for the line segment and the ROIs are positioned relative to the working estimate.

Figure 15:
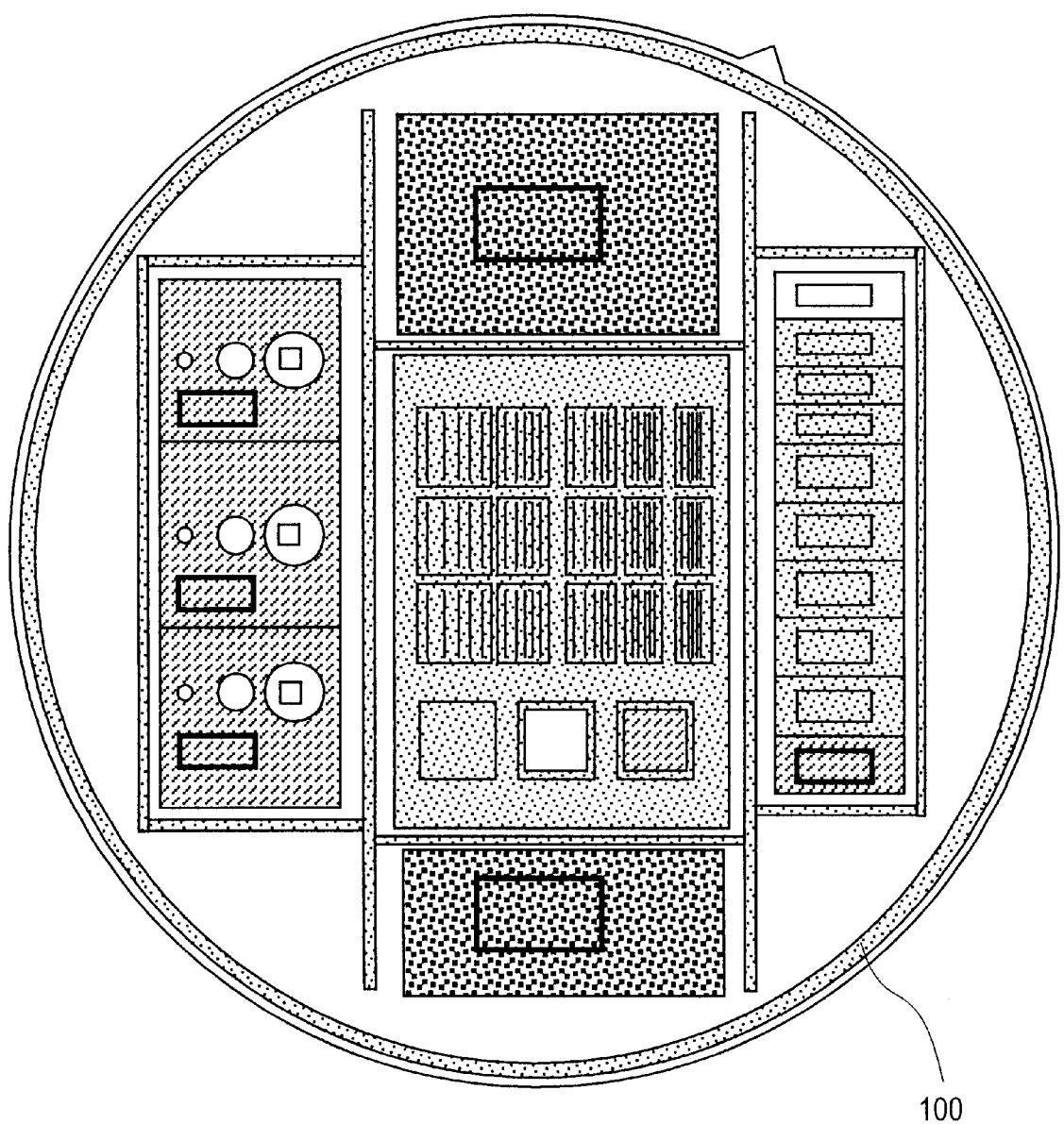
FIG. 15 illustrates the ROIs for the phantom of FIG. 1 according to a preferred embodiment of the present invention.

FIG. 15 illustrates the ROIs for the phantom 100 of FIG. 1. Each of the steps of the step intensity sub-phantom 150, each of the resolution patterns 175 of the resolution sub-phantom, and each of the regions 110–1130 of the contrast detail sub-phantom is covered by a ROI. Additionally, the high and low intensity contrast regions 180, 185 and the upper and lower meshes 190, 195 are covered by an ROI. Additional ROIs may occur outside the phantom 100. For example, the phantom 100 may be surrounded by a mesh similar to the upper and lower mesh 190, 195 which may be covered by an ROI. Processing of the imported image proceeds with step 795.

Returning to step 740 of FIG. 7, if the imported image is identified at the phantom 200 of FIG. 2, then the fiducials are located at step 755. Although the blobs corresponding to the fiducials 240 are similar in terms of blob area and blob density, individual fiducials may be distinguished based on their location relative to the midpoint of the perimeter ring 240. Once a fiducials has been located, the intersection point of the horizontal and vertical portions of the fiducial is determined at step 765. Once a fiducial has been identified, its orientation is known based on the position of the fiducial relative to the midpoint of the perimeter ring. With the knowledge of the fiducial's location and orientation, a small search area may be established surrounding the vertical and horizontal portions of the fiducial 240.

Figure 16:
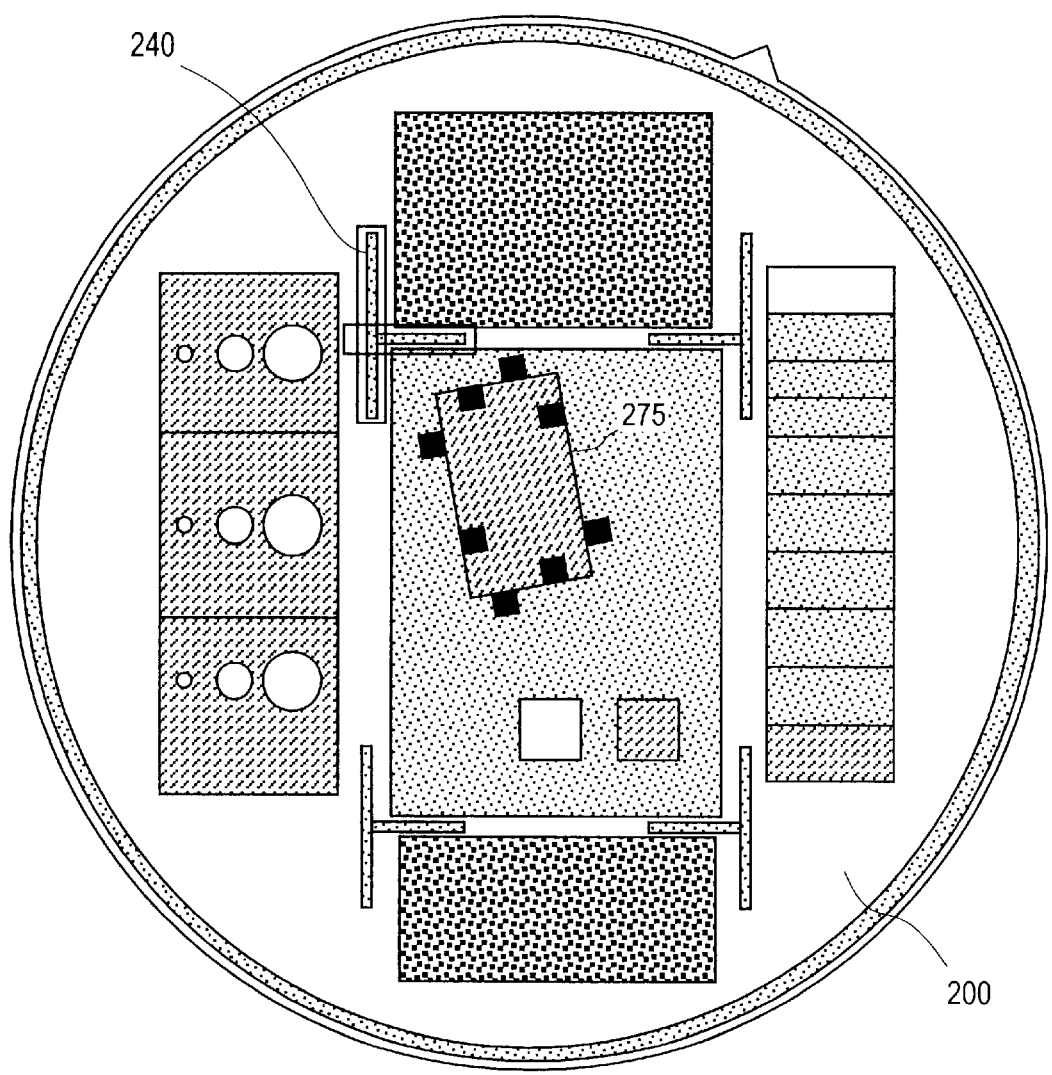
FIG. 16 illustrates the search areas surrounding the vertical and horizontal portions of the fiducials according to a preferred embodiment of the present invention.

FIG. 16 illustrates the search areas surrounding the vertical and horizontal portions of a fiducial 240. Once the vertical and horizontal components of the fiducial have been determined, the intersection of the vertical and horizontal components is known at step 765. The four intersection points provide four accurate registration points. These registration points and their corresponding points in the stored physical model of the phantom are used to determine a polynomial transformation. This polynomial transformation is then used to predict ROIs for contrast and dynamic range measurements in the phantom 200 of FIG. 2 at step 790. The ROIs for the phantom 200 of FIG. 2 are the same as the ROIs for the phantom 100 of FIG. 1 except the phantom 200 has ROIs surrounding the coupon 275.

Figure 17:
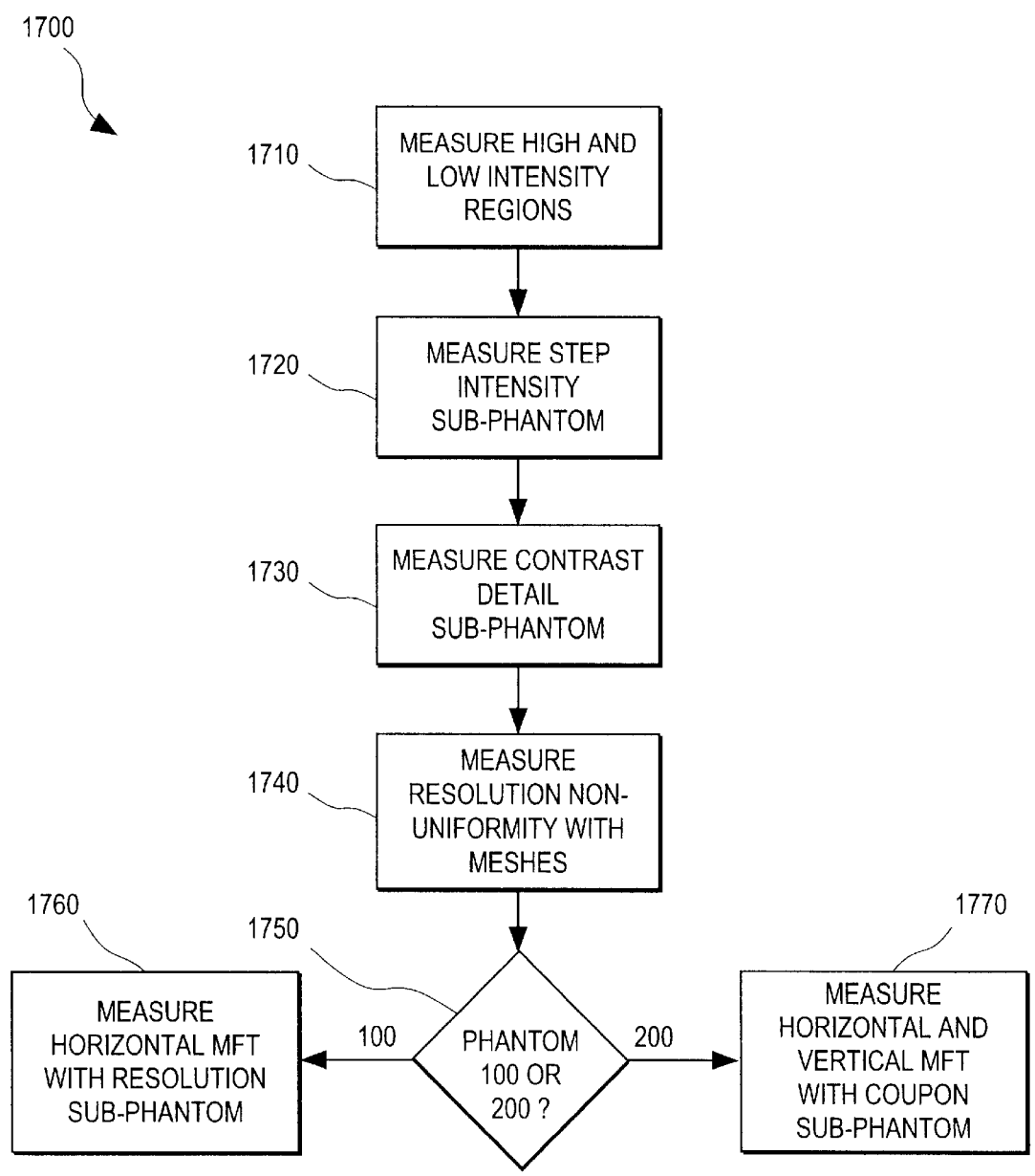
FIG. 17 illustrates a flowchart of a preferred embodiment for measuring sub-phantom parameters according to the present invention.

FIG. 17 illustrates a flowchart 1700 of a preferred embodiment for measuring sub-phantom parameters according to the present invention and step 370 of the flowchart of FIG. 3. Once the ROIs for the phantom have been determined, the high and low intensity regions 180, 185 are measured at step 1710. The high and low intensity regions provide the pixel values that correspond to the maximal and minimal amounts of received x-ray radiation and are used in the rest of the x-ray parameter measurements.

Next, at step 1720, the step-intensity sub-phantom is measured to determine the linearity of the x-ray system. The step-intensity sub-phantom is composed of linear steps of increasing thickness which should yield a linearly increasing attenuation value with increasing thickness. By comparing the pixel value of each step with its expected value and averaging the difference with respect to all steps, the accuracy of the x-ray system is determined.

Next, at step 1730, the contrast detail sub-phantom is used to measure the contrast of the x-ray system. Turning to FIG. 15, the mean value inside the small square ROIs inside the circular apertures and the mean value insides the rectangular ROIs are computed. The difference between the mean values inside the square ROIs and the rectangular ROIs is the contrast of the x-ray system. The contrast noise ratio may also be determined by dividing the contrast by the standard deviation of the pixels from inside that ROI.

Next, at step 1740, the resolution non-uniformity of the x-ray is system is determined using the upper mesh 190 and lower mesh 195. The difference in the Modulation Transfer Functions (MTFs) of the meshes divided by the mean value of the MTFs is the resolution non-uniformity.

Next, at step 1750, the type of phantom is identified. If the imported image is of the phantom 100 of FIG. 1, the system proceeds to step 1760 and the horizontal MTF is measured using the resolution patterns 175 of the resolution sub-phantom 170. The MTF is measured at 15 spatial frequencies corresponding to the following line pair groups in the resolution patterns 175: 0.50, 0.55, 0.60, 0.70, 0.80, 0.90, 1.0, 1.1, 1.2, 1.4, 1.6, 1.8, 2.0, 2.5, and 3.0 lp/mm. The MTF may be determined as:

$$MTF = (\pi * sqrt(2))/(4 * Mean0) * sqrt(VarFreq)$$

where VarFreq=|VarROI−VarNoise|, VarROI=Variance in the ROI, VarNoise=(VarBlack+VarWhite)/2, and Mean0=(MeanWhite−MeanBlack)/2. The mean and variance for the black and white regions (ROIs) are measured in high and low intensity contrast regions 180, 185.

If the imported image is of the phantom 200 of FIG. 2, the system proceeds to step 1770 and both the horizontal and vertical MTF are calculated using the coupon 275. The edge response functions for the left and right edges of the coupon 275 are used to compute horizontal MTF curves, while the edge response functions of the top and bottom edges are used to compute vertical MTF curves. For each edge of the coupon, the MTF curve is computed as follows. First the initial coordinates for the edge points along each row or column are determined. Second, a straight line is fit to the edge points. Third, the edge profiles along all the rows or columns are combined to obtain the edge response function curve. Fourth, the line spread function is obtained by differentiating the edge response function. Finally, the MTF curve is obtained by computing the Fourier transform of the line spread function. Additionally, the MTF curves for the left and right edges may be combined to obtain a more robust estimate of the horizontal MTF. Similarly, the MTF curves for the top and bottom edges may be combined to obtain a more robust estimate of the vertical MTF.

Figure 18:
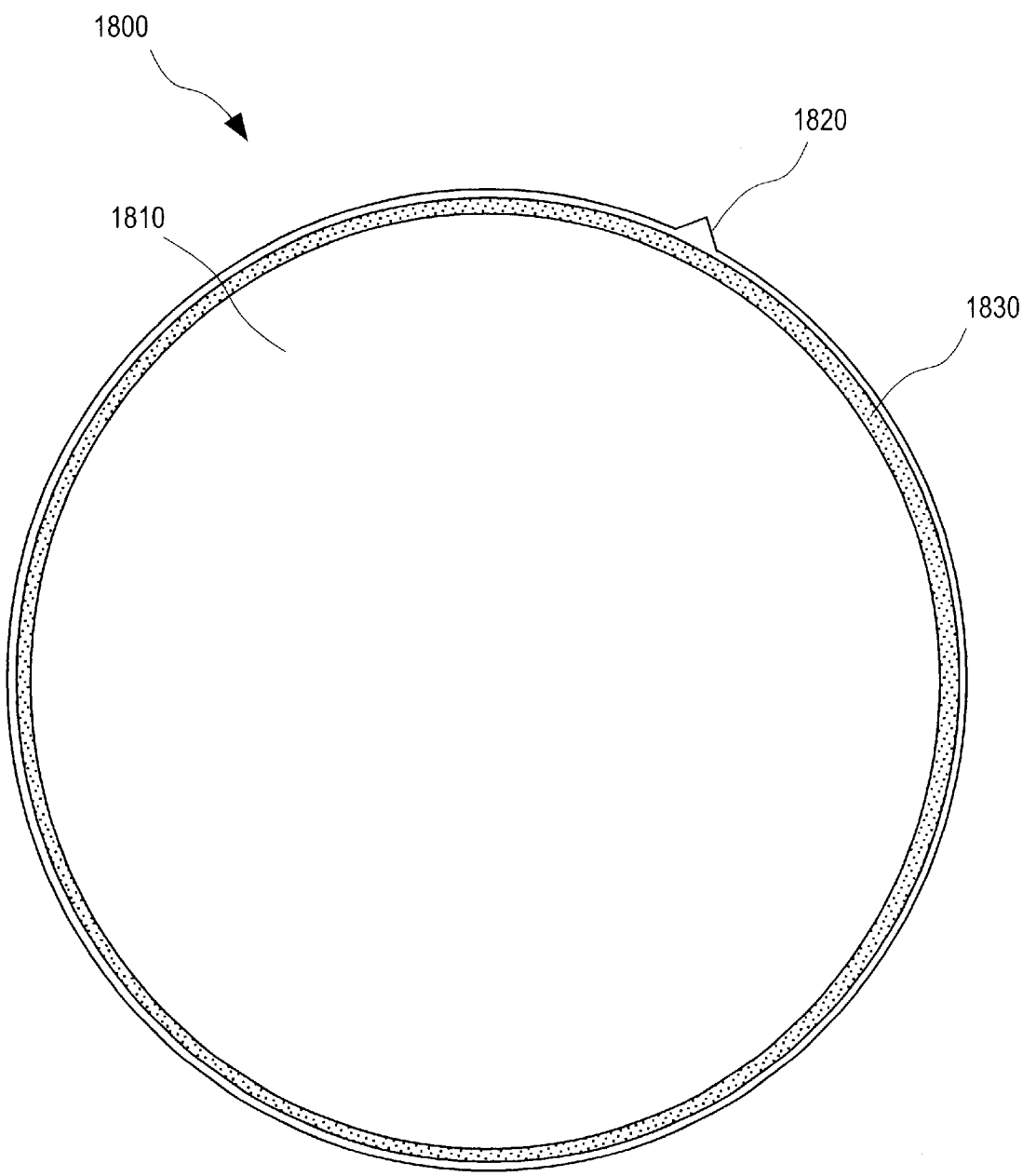
FIG. 18 illustrates a preferred embodiment of a flat-field x-ray phantom 1800 according to a preferred embodiment of the present invention.

FIG. 18 illustrates a preferred embodiment of a flat-field x-ray phantom 1800 according to a preferred embodiment of the present invention. The flat-field phantom 1800 is another type of phantom that may be employed with the x-ray image evaluation system of the present invention. The flat-field phantom 1800 includes a base 1810, a positioning tab 1820, and a perimeter ring 1830. The flat-field phantom may be comprised of a metal disk and is preferably comprised of aluminum. Alternatively, the flat-field phantom may be a uniform, square phantom.

The flat-field phantom 1800 may assist in measuring such x-ray system parameters as brightness uniformity, SNR uniformity, system noise (Noise Power Spectrum), and bad pixel artifact verification.

Brightness uniformity (BU) is a measurement of the uniformity in the imported grayscale image. To determine BU, first the mean gray levels are measured inside regions of interest (ROI) of size 3 cm×3 cm, overlapped by 1.5 cm with a 1.5 cm border around the entire image. The brightness nonuniformity(BU) measure is calculated using the ROI mean gray values. Multiple BU measurements are made for global, vertical, and horizontal as:

BU=[(Max−Min)/Mean]*100 where Max, Min, and Mean are the maximum, minimum and mean of the ROI values, respectively.

*BU H*=Max([(MaxR−MinL)/Mean],[(MaxL−MinR)/Mean])*100 where R, L represent suffixes for right and left half of image stats.

*BU V*=Max([(MaxT−MinB)/Mean],[(MaxB−MinT)/Mean])*100 where T, B represent suffixes for top and bottom half of image stats.

SNR uniformity is a measurement of the ability of the system to deliver the same SNR across the entire image. Flat field SNR uniformity is calculated by measuring the ratio between the mean value and the standard deviation in ROI's positioned across a flat field image. The mean value calculated from a single exposure image, while the standard deviation is estimated from a subtraction image of two consecutive exposures, and then normalized by sqrt(2). The size and position of the ROT's are the same as the brightness uniformity positions.

The SNR non-uniformity factor is calculated using these ratios as:

[(MaxROI−MinROI)/MeanROI]*100 where MaxROI, MinROI and MeanROI are the maximum, minimum and mean of the individual ROI's, respectively.

The system noise (Noise Power Spectrum) measures the average noise level in the flat-field image. The calculation of the system noise uses two images of the flat-field phantom 1800. To determine the system noise, first the first image is subtracted from the second image within the ROIs. Noise is corrected by dividing by sqrt(2). Next, the two-dimensional Fourier Transform is calculated, preferably with a 512-point Fast Fourier Transform (FFT). Next, a radial average of the two-dimensional noise power spectrum is performed. Finally, the average signal level is found as the arithmetic mean of each image's mean of the ROI.

Bad pixel artifact verification is determined by analyzing three images of the flat-field phantom 1800. The three images are the result of differing x-ray dosage levels such as low dose, nominal dose, and high dose levels. A histogram analysis of all pixels is conducted. The histogram width is characterized by a value of S. Pixels whose values fall outside of X*S are considered bad pixels.

As opposed to the x-ray system parameters above, composite x-ray phantoms (phantoms with multiple sub-phantoms) such as the x-ray phantom 100 of FIG. 1, may be used to measure such image quality parameters as MTF, contrast and dynamic range, for example. The tiled ROI measurements of the flat-field phantom are particularly suited to the characterization of x-ray systems with digital, solid state x-ray detectors. The flat-field measurements allow full coverage of the entire population of pixels in the detector.

Figure 19:
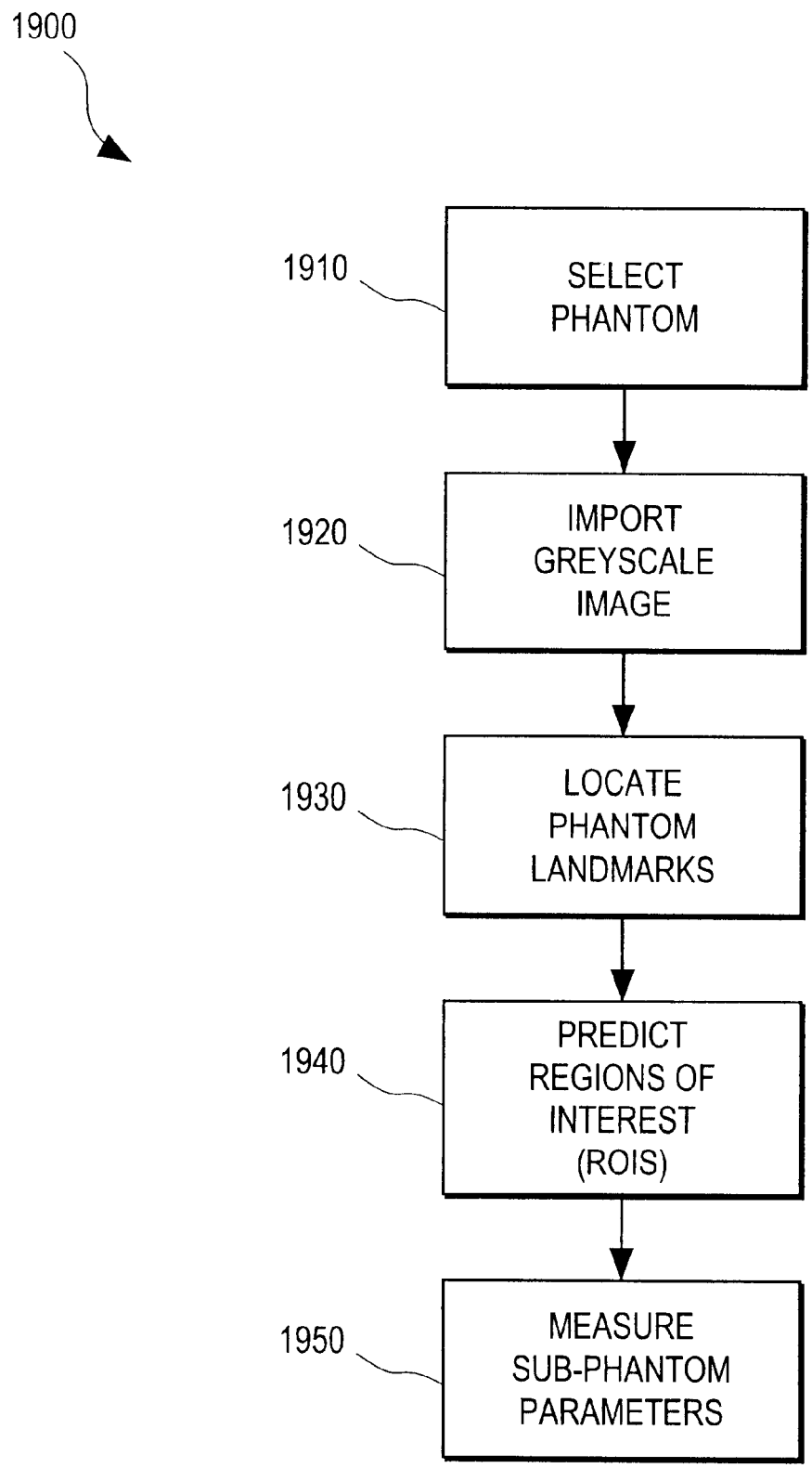
FIG. 19 illustrates a flowchart 1900 of a preferred embodiment of a semi-automated phantom image evaluation system according to the present invention.

FIG. 19 illustrates a flowchart 1900 of a preferred embodiment of a semi-automated phantom image evaluation system according to the present invention. Referring back to the flowchart 300 of the automated phantom evaluation system of FIG. 3, the process described therein determines the identity of a an unknown inserted phantom at steps 320, 330 and 340. Alternatively, the system may be configured to operate in a semi-automated fashion, as illustrated in the flowchart 1900, such that a user may enter the phantom in use into the system instead of the system automatically determining the phantom. The user may select the phantom in use by manual selection or by selection through a computer interface, for example.

In the flowchart 1900, first the user selects the inserted phantom from the database or bank of possible phantoms at step 1910. Next, at step 1920, the grayscale image is imported into the phantom image evaluation system. Because the user has selected the inserted phantom, the expected components, landmarks, and ROIs of the inserted phantom are known. Process steps 1930–1950 proceed as in the flowchart 300 of FIG. 3 using the known ROI locations from the phantom bank.

FIG. 20 illustrates a flowchart 2000 of a preferred embodiment of a system for adding a phantom template to a database or bank of phantom templates according to the present invention. A phantom template may be added to the system for any current or future commercially available phantom. Once the phantom template has been added to the system, the phantom corresponding to the template may be identified when inserted and used to analyze the x-ray system. The present image quality evaluation system is thus expandable to any phantom and is not limited to the x-ray phantoms 100–200 of FIGS. 1 and 2 or the flat-field phantom 1800 of FIG. 18.

Referring to the flowchart 2000, first, at step 2005, a unique identifier is chosen for the phantom template to be added to the system. Next, at step 2010, the identifier is assigned an abstract phantom object. The object includes data structures to hold the identifying attributes of the new phantom template. Next, at step 2015, the geometric attributes of the new phantom template are added to the object. The attributes may include the size and location of each component of the phantom. The ROIs of the phantom are also added to the phantom object. The geometric attributes and the ROIs may be added using basic pre-defined data members such as boxes, lines, polygons, circles, and points. Next, at step 2020, the landmarks are identified within the x-ray image of the phantom. The landmarks may be isolated regions corresponding to high contrast components or high contrast line segments, for example. Next, at step 2025, methods are defined to discriminate or classify each landmark on the x-ray image of the phantom. Heuristic rules based on the unique attributes of each landmark are used. For example, the absolute or relative size of the landmark or the landmark's locations, aspect ration, density or orientation, for example, may be used. Next, at step 2030, registration points that may be accurately localized are identified on some or all of the landmarks. For example, points on line segments, intersection points of line segments, or the center of gravity of symmetric landmarks, for example, may be used as registration points. Next, at step 2035, The registration points are added to the phantom object as an appropriate data member such as a vector of x-y co-ordinates, for example. Next, at step 2040, methods are defined to accurately localize the registration points within an image. For example, the registration points may be localized by computing the mathematical intersection point of two line segments. Next, at step 2045, methods are defined to determine the location of ROIs corresponding to high contrast components. For example, an ROI inside a rectangular lead (PB) block. Next, at step 2050, geometric transformations are defined to predict the location of ROIs corresponding to low contrast components. For example, the geometric transformation may be polynomial warping based on registration points. Next, at step 2055, methods to compute image quality parameters based on analysis of the ROIs are defined. Finally, at step 2060, the new phantom template object is added to the list of phantom templates in the phantom database or bank. The list of phantom templates in the bank is known by a phantom template manage object which may retrieve and apply any desired phantom template. In particular, the model or template for new custom-made or off-the-shelf phantoms may be created and added to the system.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features which come within the spirit and scope of the invention.

What is claimed is:

1. A method for automated image quality evaluation of x-ray imaging systems, said method comprising:
    processing an imported x-ray image to determine image components;
    locating landmarks in an area of said imported x-ray image exposed to x-rays;
    predicting regions of interest in said area of said imported x-ray image exposed to x-rays based on said landmarks;
    measuring image quality parameters within said regions of interest for evaluation of x-ray imaging system image quality; and
    adjusting said image quality parameters based on said evaluation of x-ray imaging system image quality.

2. The method of claim 1 further comprising matching image components in said imported x-ray image to expected image components in a predetermined phantom template to predict said regions of interest.

3. The method of claim 2, further comprising rejecting imported images not matching said expected landmarks in a phantom template.

4. The method of claim 2 further comprising adding a template for a new custom-made or off-the-shelf x-ray phantom.

5. The method of claim 1 further comprising predicting said regions of interest based on comparing the locations of said landmarks in said imported x-ray image to the location of landmarks within a predetermined phantom template.

6. The method of claim 1 further comprising locating image registration points based on said landmarks.

7. The method of claim 6 further comprising predicting regions of interest based on said image registration points.

8. The method of claim 1, further comprising creating an image histogram and determining a threshold based on said histogram.

9. The method of claim 8, wherein said threshold is determined based on a position of two peak regions in the said histogram.

10. The method of claim 8, further comprising binarizing said imported image based on said threshold.

11. The method or claim 1, further comprising using connected component analysis to determine components in said imported image.

12. The method of claim 1, further comprising determining at least one of the midpoint and radius of a metallic perimeter ring of said imported image.

13. The method of claim 1 further comprising locating at least one of vertical and horizontal line segments in said imported image.

14. The method of claim 1 further comprising locating at least one fiducial in said imported image.

15. The method of claim 1 further comprising locating at least one rectangular, high contrast component in said imported x-ray image.

16. The method of claim 1, further comprising measuring at least one of a horizontal Modulation Transfer Function (MTF) and a vertical MTF using a coupon sub-phantom in said imported image.

17. The method of claim 1, further comprising measuring a resolution non-uniformity of an x-ray system using at least one mesh area in said imported image.

18. An automated image quality evaluation system including:
    a phantom having at least one sub-phantom for assisting in the determination of at least one system performance parameter, and
    an image processor for analyzing an x-ray image of said phantom, wherein said image processor identifies said at least one sub-phantom based on at least on a landmark in said at least one sub-phantom, wherein said image processor predicts a region of interest in said at least one sub-phantom based on said at least one landmark.

19. The evaluation system of claim 18, wherein said image processor determination image components in said x-ray image.

20. The evaluation system of claim 18, wherein said image processor locates phantom landmarks in said x-ray image.

21. The evaluation system of claim 18, wherein said image processor predicts regions of interest in said x-ray image.

22. The evaluation system of claim 18, wherein said image processor measures at least one image quality parameter based on one sub-phantom.

23. A method for automated image quality evaluation using phantom images from a medical imaging system, comprising: obtaining a grayscale image representative of a phantom mounted in the medical imaging system;
    analyzing said grayscale image with respect to a predetermined phantom template corresponding to a desired image of said phantom in order to evaluate said grayscale image; and automatically determining whether to reject said grayscale image.

24. The method of claim 23, further comprising:
    determining components of said grayscale image, said components used in said analyzing step to evaluate said grayscale image.

25. The method of claim 23, further comprising:
    comparing components of said grayscale image with associated components of said phantom template to evaluate said grayscale image.

26. The method of claim 23, further comprising:
    locating landmark in said grayscale image based on predetermined configurations for said phantom mounted in the medical imaging systems.

27. The method of claim 23, further comprising:
    predicting regions of interest in said grayscale image based on predefined characteristics of said phantom mounted in the medical imaging system.

28. The method of claim 23, further comprising:
    measuring sub-phantom parameters representation of regions of interest from said phantom mounted in the medical imaging system.

29. The method of claim 23, further comprising:
creating a histogram of said grayscale image to evaluate said grayscale image.

30. The method of claim 23, further comprising:
comparing an imaging characteristic of said grayscale image to at least one threshold to determine whether to reject said grayscale image.

31. A method for determining a phantom template for an automated image quality evaluation system comprising:
identifying a phantom to be template;
determining geometric attributes of the said phantom;
determining landmark characteristics of said phantom;
determining the registration points of said phantom;
predicting regions of interest of said phantom; and
storing said geometric attributes, landmarks, registration points, and regions of interest to form a phantom template for said phantom said phantom template capable of use in image quality evaluation.

32. The method of claim 31, further comprising generating geometric transformations based on said registration points to predict the location of at least one region of interest.

33. The method of claim 32, wherein said geometric transformation includes polynomial warping.

34. The method of claim 31, wherein said registration points are at least one of points on a line segment, intersection points of line segments, and the center of gravity of symmetric landmarks.

* * * * *

UNITED STATES PATENT AND TRADEMARK OFFICE
CERTIFICATE OF CORRECTION

PATENT NO.    : 6,694,047 B1
DATED         : February 17, 2004
INVENTOR(S)   : Farrokhnia et al.

It is certified that error appears in the above-identified patent and that said Letters Patent is hereby corrected as shown below:

Column 4,
Line 5, delete "1800"
Line 7, delete "1900"
Line 10, delete "2000"

Column 5,
Line 37, delete "mm." and substitute therefor -- mm, --

Column 8,
Line 45, delete "pf" and substitute therefor -- of --

Column 9,
Line 24, delete "440" and substitute therefor -- 430 --

Column 12,
Line 65, delete "that" and substitute therefor -- where --

Column 12,
Line 65, delete "that" and substitute therefor -- where --

Column 14,
Lines 21-27, should not be indented

Column 18,
Lines 41 and 46, ":" insert new paragraph
Line 57, delete "landmark" and substitute therefor -- landmarks --

Column 19,
Line 10, delete "template" and substitute therefor -- templated --
Lines 11 and 13, delete "the"

UNITED STATES PATENT AND TRADEMARK OFFICE
CERTIFICATE OF CORRECTION

PATENT NO. : 6,694,047 B1
DATED : February 17, 2004
INVENTOR(S) : Farrokhnia et al.

It is certified that error appears in the above-identified patent and that said Letters Patent is hereby corrected as shown below:

Column 20,
Line 3, after the word "phantom" insert -- , --

Signed and Sealed this

Twenty-second Day of February, 2005

JON W. DUDAS
*Director of the United States Patent and Trademark Office*